(12) United States Patent
Penny et al.

(10) Patent No.: US 7,300,436 B2
(45) Date of Patent: Nov. 27, 2007

(54) TISSUE RESURFACING

(75) Inventors: Keith Penny, Monmouth (GB); Nigel Mark Goble, Hungerford (GB)

(73) Assignee: Rhytec Limited, Berkshire (GB)

(*) Notice: Subject to any disclaimer, the term of this patent is extended or adjusted under 35 U.S.C. 154(b) by 513 days.

(21) Appl. No.: 11/000,417

(22) Filed: Dec. 1, 2004

(65) Prior Publication Data

US 2005/0149012 A1  Jul. 7, 2005

Related U.S. Application Data

(63) Continuation-in-part of application No. 10/792,765, filed on Mar. 5, 2004, which is a continuation-in-part of application No. 09/789,550, filed on Feb. 22, 2001, now Pat. No. 6,723,091.

(60) Provisional application No. 60/183,785, filed on Feb. 22, 2000.

(30) Foreign Application Priority Data

Nov. 23, 2004 (GB) .................... 0425765.5

(51) Int. Cl.
*A61B 18/18* (2006.01)
(52) U.S. Cl. .............. 606/34; 606/41; 606/48
(58) Field of Classification Search ......... 606/32–34, 606/37–42, 45–50
See application file for complete search history.

(56) References Cited

U.S. PATENT DOCUMENTS

| 2,909,735 | A | 10/1959 | Hessler, Jr. |
| 3,280,362 | A | 10/1966 | Ohtomo |
| 3,699,967 | A | 10/1972 | Anderson |
| 3,838,242 | A | 9/1974 | Goucher |
| 3,903,891 | A | 9/1975 | Brayshaw |
| 4,040,426 | A | 8/1977 | Morrison, Jr. |
| 4,781,175 | A | 11/1988 | McGreevy et al. |
| 4,839,492 | A | 6/1989 | Bouchier et al. |
| 4,901,719 | A | 2/1990 | Trenconsky et al. .......... 606/49 |

(Continued)

FOREIGN PATENT DOCUMENTS

DE        35 21 616 A1   12/1986

(Continued)

OTHER PUBLICATIONS

Pelah I. et al., "Differential calorimeter for measurement of absorbed energy in laser-produced plasmas", Review of Scientific Instruments USA, vol. 48, No. 8, Aug. 1977, pp. 1068-1071.

(Continued)

*Primary Examiner*—Michael Peffley
(74) *Attorney, Agent, or Firm*—Oliff & Berridge, PLC

(57) ABSTRACT

A method for skin treatment comprises the steps of delivering at least one pulse of radio frequency power to at least one electrode in order to create an electric field; passing gas through the electric field in order to form plasma from the gas; and applying the plasma to the surface of skin. The amount of radio frequency power may be relatively low such that the application of plasma causes denaturation of collagen within the collagen-containing tissue beneath the skin surface, which may promote the generation of new collagen within the collagen-containing tissue.

15 Claims, 15 Drawing Sheets

U.S. PATENT DOCUMENTS

| | | | |
|---|---|---|---|
| 5,364,392 A | 11/1994 | Warner et al. ............... 606/34 |
| 5,383,874 A * | 1/1995 | Jackson et al. ............... 606/1 |
| 5,400,267 A | 3/1995 | Denen et al. |
| 5,669,904 A | 9/1997 | Platt, Jr. et al. |
| 5,669,907 A | 9/1997 | Platt, Jr. et al. |
| 5,697,281 A | 12/1997 | Eggers et al. |
| 5,742,718 A | 4/1998 | Harman et al. |
| 5,755,753 A | 5/1998 | Knowlton |
| 5,843,019 A | 12/1998 | Eggers et al. |
| 5,888,198 A | 3/1999 | Eggers et al. |
| 5,948,011 A | 9/1999 | Knowlton |
| 5,968,034 A | 10/1999 | Fullmer et al. |
| 6,024,733 A | 2/2000 | Eggers et al. |
| 6,053,172 A | 4/2000 | Hovda et al. |
| 6,063,084 A | 5/2000 | Farin |
| 6,099,523 A | 8/2000 | Kim et al. |
| 6,135,998 A | 10/2000 | Palanker |
| 6,149,620 A | 11/2000 | Baker et al. |
| 6,159,194 A | 12/2000 | Eggers et al. |
| 6,165,169 A * | 12/2000 | Panescu et al. ............... 606/1 |
| 6,190,381 B1 | 2/2001 | Olsen et al. |
| 6,210,402 B1 | 4/2001 | Olsen et al. |
| 6,213,999 B1 | 4/2001 | Platt, Jr. et al. |
| 6,228,078 B1 | 5/2001 | Eggers et al. |
| 6,296,636 B1 | 10/2001 | Cheng et al. |
| 6,309,387 B1 | 10/2001 | Eggers et al. |
| 6,387,092 B1 | 5/2002 | Burnside et al. |
| 6,413,253 B1 | 7/2002 | Koop et al. |
| 6,443,948 B1 | 9/2002 | Suslov |
| 6,464,689 B1 | 10/2002 | Qin et al. |
| 6,475,215 B1 | 11/2002 | Tanrisever |
| 6,518,538 B2 | 2/2003 | Bernabei |
| 6,565,558 B1 | 5/2003 | Lindenmeier et al. |
| 6,582,427 B1 | 6/2003 | Goble et al. |
| 6,920,312 B1 | 7/2005 | Benjamin |
| 7,118,564 B2 * | 10/2006 | Ritchie et al. ............... 606/16 |
| 2001/0034519 A1 | 10/2001 | Goble et al. |
| 2002/0043520 A1 | 4/2002 | Bernabei |
| 2002/0161362 A1 | 10/2002 | Penny et al. |
| 2003/0069576 A1 | 4/2003 | Tanrisever |
| 2003/0125727 A1 | 7/2003 | Truckai |
| 2004/0044342 A1 | 3/2004 | Mackay |
| 2004/0186470 A1 | 9/2004 | Goble et al. |
| 2005/0149012 A1 | 7/2005 | Penny et al. |
| 2005/0256519 A1 | 11/2005 | Goble et al. |

FOREIGN PATENT DOCUMENTS

| | | |
|---|---|---|
| EP | 0 250 202 A2 | 12/1987 |
| EP | 0 315 400 A2 | 5/1989 |
| EP | 0 353 178 | 1/1990 |
| EP | 0 680 771 A1 | 11/1995 |
| EP | 0 787 465 A1 | 8/1997 |
| EP | 0 901 290 A1 | 3/1999 |
| EP | 0 951 921 A2 | 10/1999 |
| FR | 2 699 785 | 6/1994 |
| JP | 09299379 A2 | 11/1997 |
| JP | 09299380 A2 | 11/1997 |
| JP | 10024048 A2 | 1/1998 |
| JP | 10024050 A2 | 1/1998 |
| JP | 10286316 A2 | 10/1998 |
| RU | 2138213 C1 | 9/1999 |
| WO | WO89/07921 | 9/1989 |
| WO | WO95/00759 | 1/1995 |
| WO | WO95/24111 | 9/1995 |
| WO | WO95/26686 | 10/1995 |
| WO | WO98/35618 | 8/1998 |
| WO | WO 00/32127 | 6/2000 |
| WO | WO 00/53112 | 9/2000 |
| WO | WO16219 | 8/2001 |
| WO | WO 2005/084569 A1 | 9/2005 |

OTHER PUBLICATIONS

Kulik P. et al., "Method for Measurement of Thermal-Flux Distribution in Low-Temperature Plasma", Instruments and Experimnetal Techniques, Consultants Bureau, New York, vol. 31, No. 2, Part 2, Mar. 1, 1988, pp. 410-412.

* cited by examiner

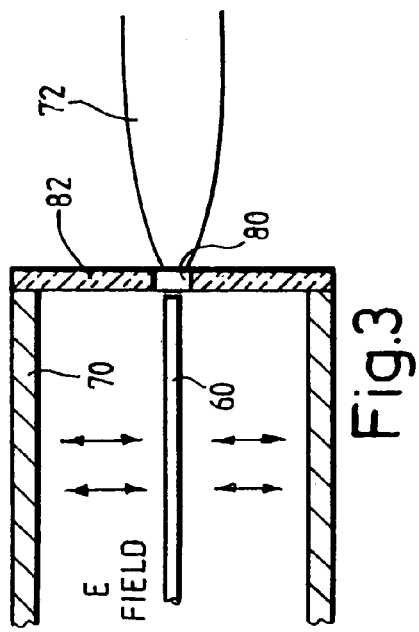
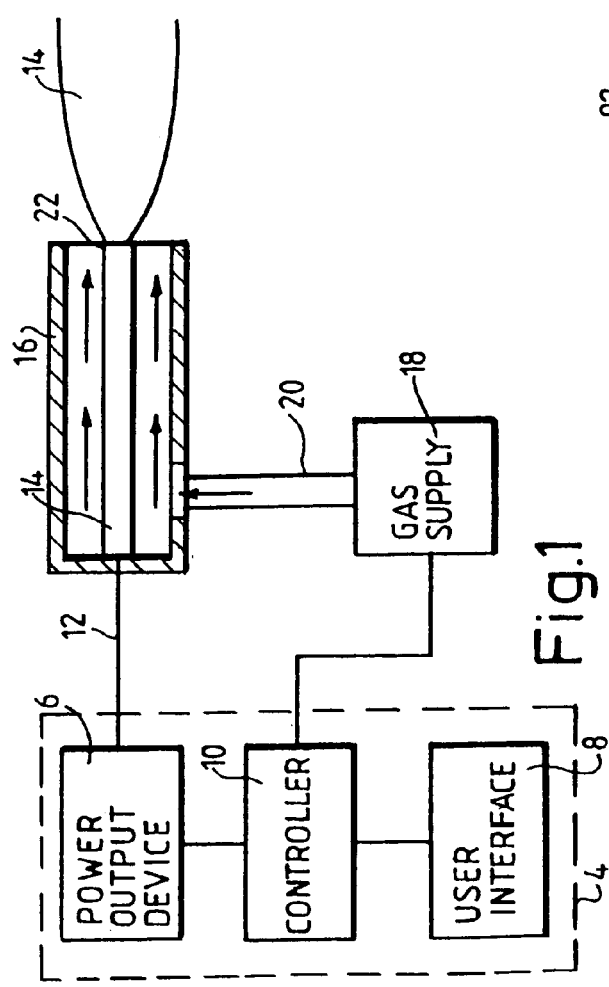
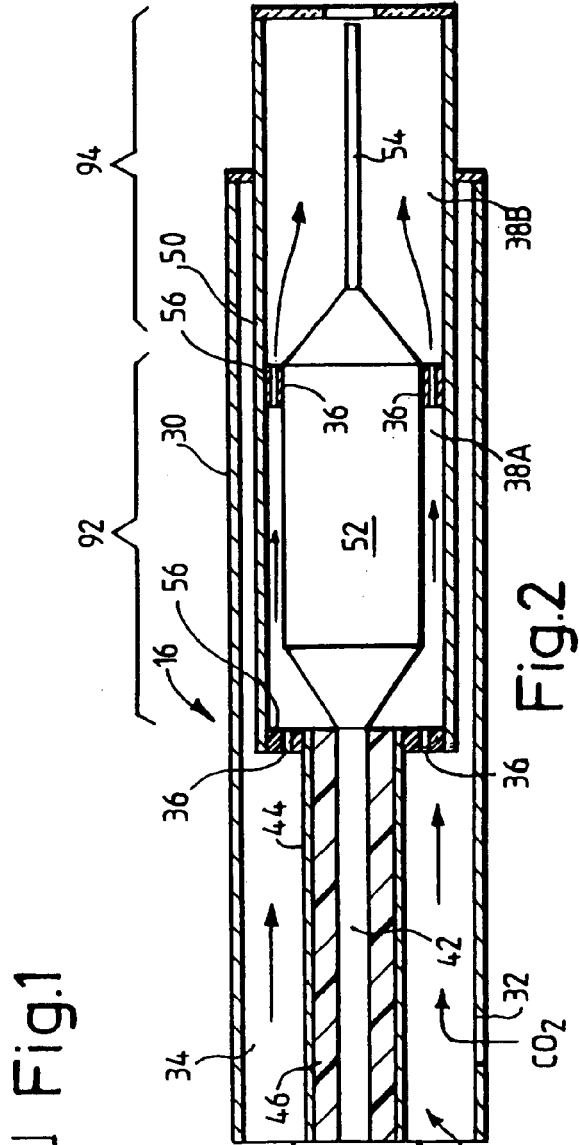

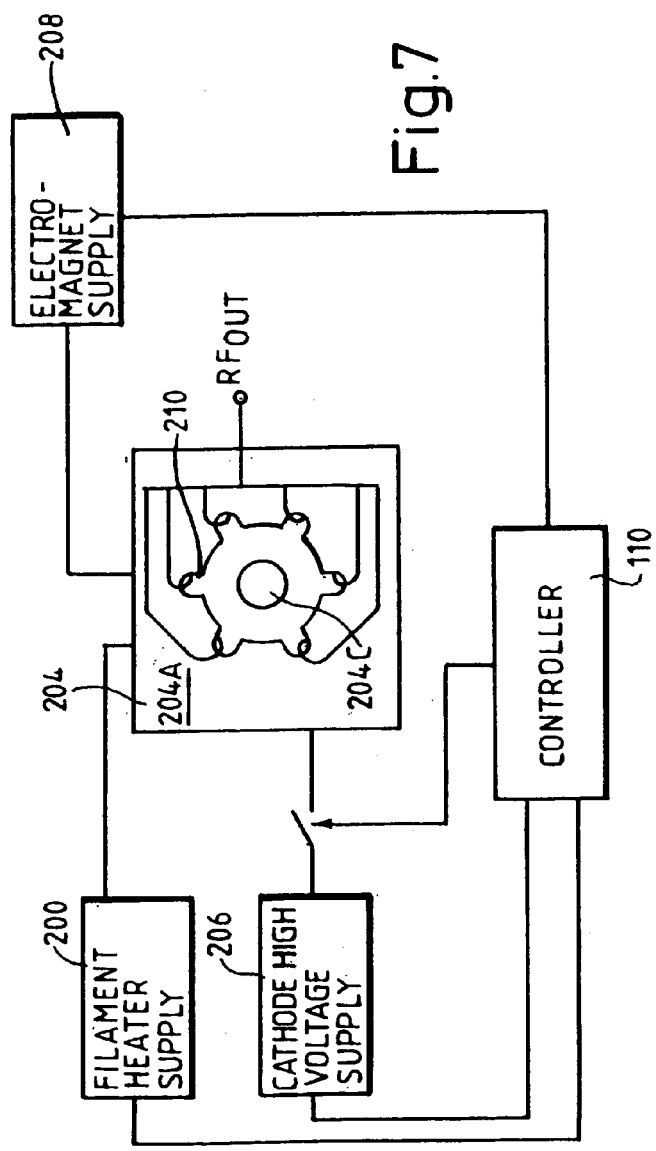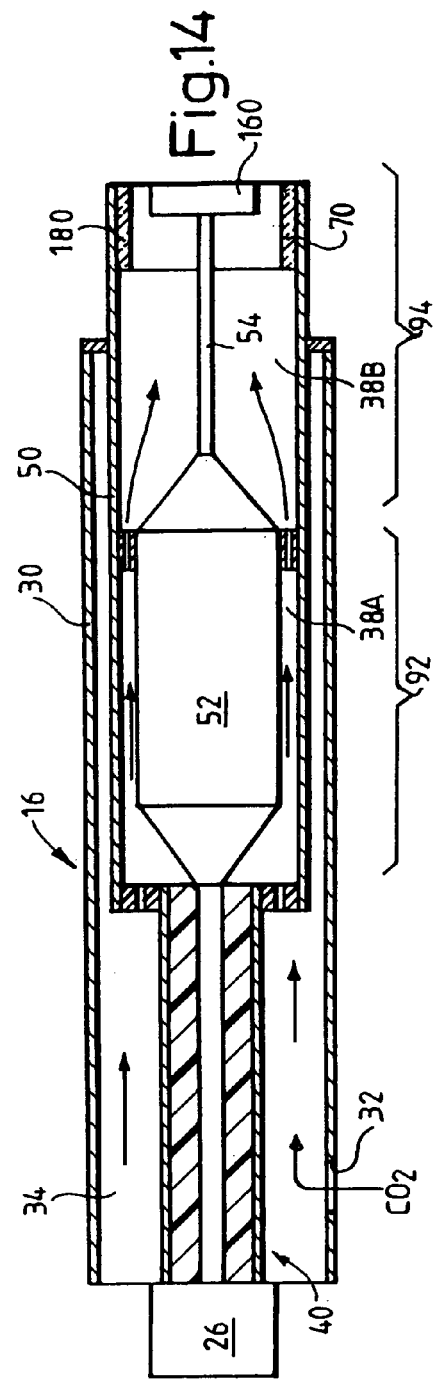

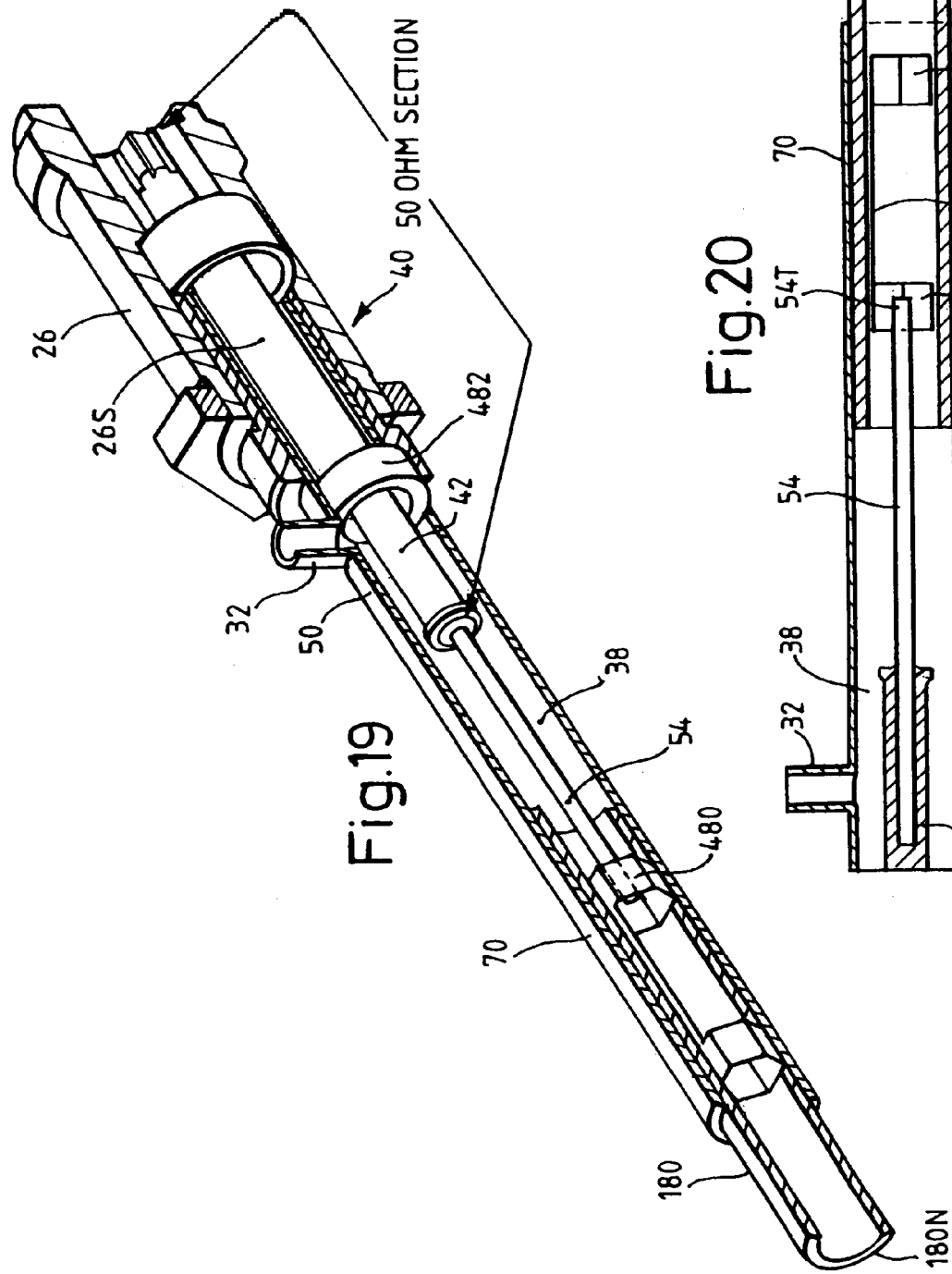

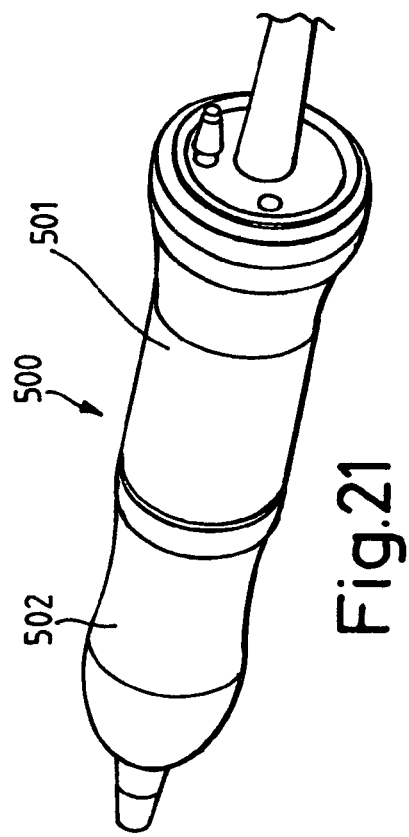
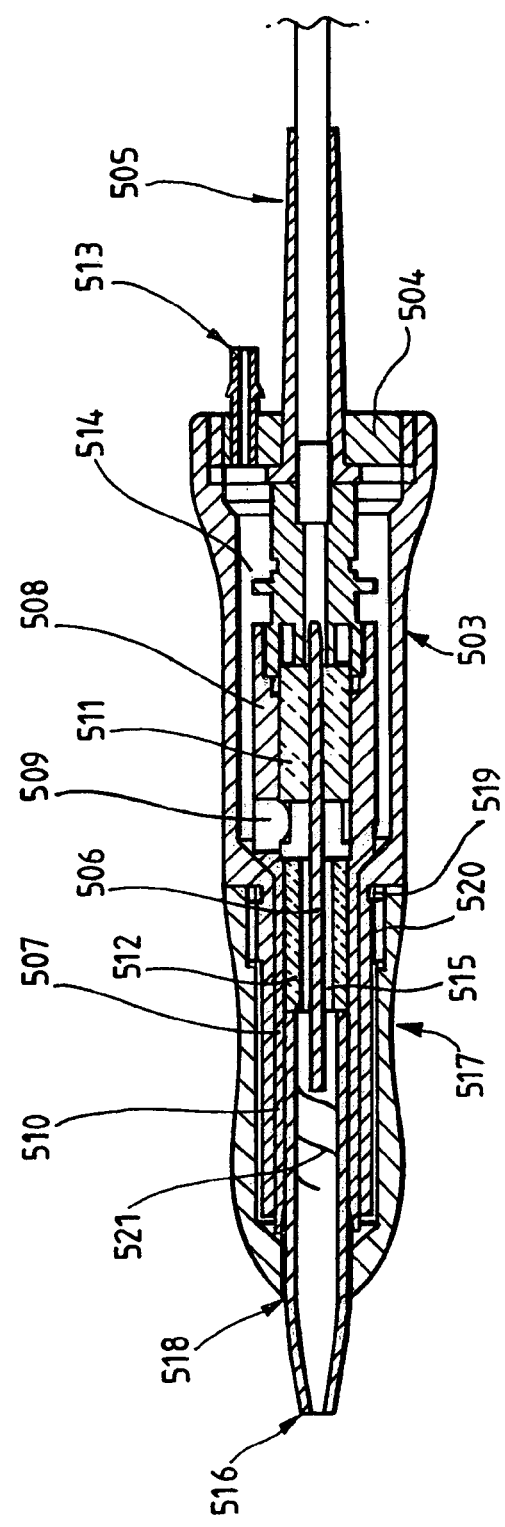

TISSUE RESURFACING

RELATED APPLICATIONS

This application is a Continuation-in-Part of U.S. patent application Ser. No 10/792,765 filed Mar. 5 2004, which in turn is a Continuation-in-Part of U.S. patent application Ser. No. 09/789,550 (now U.S. Pat. No. 6,723,091), filed Feb. 22, 2001, which in turn claims the benefit of priority of Provisional Application No. 60/183,785, filed Feb. 22, 2000.

BACKGROUND OF THE INVENTION

1. Field of Invention

This invention relates to tissue resurfacing, for example, skin resurfacing, or the resurfacing or removal of tissue located within, e.g., the alimentary canal, respiratory tracts, blood vessels, uterus or urethra.

2. Description of Related Art

Human skin has two principal layers: the epidermis, which is the outer layer and typically has a thickness of around 120μ in the region of the face, and the dermis which is typically 20-30 times thicker than the epidermis, and contains hair follicles, sebaceous glands, nerve endings and fine blood capillaries. By volume the dermis is made up predominantly of the protein collagen.

A common aim of many cosmetic surgical procedures is to improve the appearance of a patient's skin. For example, a desirable clinical effect in the field of cosmetic surgery is to provide an improvement in the texture of ageing skin and to give it a more youthful appearance. These effects can be achieved by the removal of a part or all of the epidermis, and on occasions part of the dermis, causing the growth of a new epidermis having the desired properties. Additionally skin frequently contains scar tissue, the appearance of which is considered by some people to be detrimental to their attractiveness. The skin structure which gives rise to scar tissue is typically formed in the dermis. By removing the epidermis in a selected region and resculpting the scar tissue in the dermis it is possible to improve the appearance of certain types of scars, such as for example scars left by acne. The process of removing epidermal and possibly dermal tissue is known as skin resurfacing or dermabrasion.

One known technique for achieving skin resurfacing includes the mechanical removal of tissue by means of an abrasive wheel, for example. Another technique is known as a chemical peel, and involves the application of a corrosive chemical to the surface of the epidermis, to remove epidermal, and possibly dermal skin cells. Yet a further technique is laser resurfacing of the skin. Lasers are used to deliver a controlled amount of energy to the epidermis. This energy is absorbed by the epidermis causing necrosis of epidermal cells. Necrosis can occur either as a result of the energy absorption causing the temperature of the water in the cells to increase to a level at which the cells die, or alternatively, depending upon the frequency of the laser light employed, the energy may be absorbed by molecules within the cells of the epidermis in a manner which results in their dissociation. This molecular dissociation kills the cells, and as a side effect also gives rise to an increase in temperature of the skin.

Typically during laser resurfacing a laser beam is directed at a given treatment area of skin for a short period of time (typically less than one millisecond). This can be achieved either by pulsing the laser or by moving the laser continuously and sufficiently quickly that the beam is only incident upon a given area of skin for a predetermined period of time. A number of passes be may made over the skin surface, and dead skin debris is usually wiped from the skin between passes. Lasers currently employed for dermabrasion include a $CO_2$ laser, and an Erbium-YAG laser. The mechanisms by which energy is absorbed by the tissue causing it to die, and the resultant clinical effects obtained, such as the depth of tissue necrosis and the magnitude of the thermal margin (i.e. the region surrounding the treated area that undergoes tissue modification as a result of absorbing heat) vary from one laser type to another. Essentially, however, the varying treatments provided by these lasers may be considered as a single type of treatment method in which a laser is used to impart energy to kill some or part of the epidermis (and depending upon the objective of the treatment, possibly part of the dermis), with the objective of creating growth of a new epidermis having an improved appearance, and also possibly the stimulation of new collagen growth in the dermis.

Other prior art references of background interest to the present invention include U.S. Pat. No. 3,699,967 (Anderson), U.S. Pat. No. 3,903,891 (Brayshaw), U.S. Pat. No. 4,040,426 (Morrison), U.S. Pat. No. 5,669,904, WO95/0759, WO95/26686 and WO98/35618.

SUMMARY OF THE INVENTION

The present invention provides an alternative to known skin resurfacing techniques, apparatus and methods of operating such apparatus.

According to a first aspect of the present invention, a tissue resurfacing system comprises: a surgical instrument having a gas conduit terminating in a plasma exit nozzle, and an electrode associated with the conduit, and a radio frequency power generator coupled to the instrument electrode and arranged to deliver radio frequency power to the electrode in single or series of treatment pulses for creating a plasma from gas fed through the conduit, the pulses having durations in the range of from 2 ms to 100 ms.

The application of an electric field to the gas in order to create the plasma may take place at any suitable frequency, including the application of standard electrosurgical frequencies in the region of 500 kHz or the use of microwave frequencies in the region of 2450 MHz, the latter having the advantage that voltages suitable for obtaining the plasma are more easily obtained in a complete structure. The plasma may be initiated or "struck" at one frequency, whereupon optimum power transfer into the plasma may then take place at a different frequency.

In one embodiment a radio frequency oscillating voltage is applied to the electrode in order to create a correspondingly oscillating electric field, and the power transferred to the plasma is controlled by monitoring the power reflected from the electrode (this providing an indication of the fraction of the power output from the power output device which has been transferred into the plasma), and adjusting the frequency of the oscillating voltage from the generator accordingly. As the frequency of the oscillating output from the generator approaches the resonant frequency of the electrode (which is affected by the presence of the plasma), the power transferred to the plasma increases, and vice versa.

Preferably, in this embodiment, a dipole electric field is applied to the gas between a pair of electrodes on the instrument which are connected to opposing output terminals of the power output device.

In an alternative aspect of the invention a DC electric field is applied, and power is delivered into the plasma from the DC field.

The gas employed is preferably non-toxic, and more preferably readily biocompatible to enable its natural secretion or expulsion from the body of the patient. Carbon dioxide is one preferred gas, since the human body automatically removes carbon dioxide from the bloodstream during respiration. Additionally, a plasma created from carbon dioxide is hotter (albeit more difficult to create) than a plasma from, for example argon, and carbon dioxide is readily available in most operating theatres. Nitrogen or even air may also be used.

According to another aspect of the invention, a gas plasma tissue resurfacing instrument comprises: an elongate gas conduit extending from a gas inlet to an outlet nozzle and having a heat resistant dielectric wall; a first electrode located inside the conduit; a second electrode located on or adjacent an outer surface of the dielectric wall in registry with the first electrode; and an electrically conductive electric field focussing element located inside the conduit and between the first and second electrodes.

Some preferred features are set out in the accompanying dependent claims. The system described hereinafter has the benefit of being able to produce rapid treatment at the tissue surface while minimising unwanted effects, e.g. thermal effects, at a greater than required depth.

A further aspect of the present invention provides a method of skin resurfacing at least the epidermis of a patient using a surgical system comprising an instrument having an electrode connected to a power output device, the method comprising the steps of: operating the power output device to create an electric field in the region of the electrode; directing a flow of gas through the electric field, and generating, by virtue of the interaction of the electric field with the gas, a plasma; controlling power transferred into the plasma from the electric field; directing the plasma onto the tissue for a predetermined period of time, and vaporising at least a part of the epidermis as a result of the heat delivered to the epidermis from the plasma.

The invention also provides, according to a further aspect, a tissue resurfacing system comprising: a plasma treatment instrument having a gas conduit terminating in a plasma exit nozzle, and an electrode associated with the conduit, and a radio frequency power generator coupled to the instrument electrode and arranged to deliver radio frequency power to the electrode in a single or series of treatment pulses each comprising a burst of radio frequency oscillations, the generator including a controller which operates to control the width of the treatment pulses to a predetermined width. The controller is preferably arranged to adjust the treatment pulse width by generating corresponding control pulses which are fed to a radio frequency power stage of the generator to alter the level of the power stage output from a substantially quiescent level to a predetermined, preferably constant, output power level for time periods each equal to a demanded pulse width, whereby a gas plasma is produced for such time periods. The time periods and/or the power level may be adjusted by the controller to yield metered treatment pulses for the instrument each having a predetermined total energy content.

It is possible, within the scope of the invention, for the radio frequency power output to be modulated (100% modulation or less) within each treatment pulse.

Treatment pulse widths of from 2 ms to 100 ms are contemplated, and are preferably within the range of from 3 ms to 50 ms or, more preferably, from 4 ms to 30 ms. In the case where they are delivered in series, the treatment pulses may have a repetition rate of 0.5 Hz to 10 Hz or 15 Hz, preferably 1 Hz to 6 Hz.

From an instrument aspect, the invention also provides a gas plasma tissue resurfacing instrument comprising an elongate gas conduit extending from a gas inlet to a plasma exit nozzle, at least a pair of mutually adjacent electrodes for striking a plasma from gas within the conduit, and, between the electrodes, a solid dielectric wall formed from a material having a relative dielectric constant greater than unity (preferably of the order of 5 or higher). Advantageously the conduit is formed at least in part as a dielectric tube of such material, the electrode comprising an inner electrode inside the tube and a coaxial outer electrode surrounding the tube.

Other aspects of the invention include the following:

A method of operating a surgical system is provided comprising a power output device which generates an output signal at an output terminal, a controller capable of receiving input signals from a user and controlling the power output device accordingly, an instrument having at least one electrode connected to the generator output terminal via a feed structure, a supply of gas and a further feed structure for conveying the gas from the supply to the instrument, the method comprising the steps of receiving input signals from a user, and operating the controller to determine from the user input signals a manner in which the power output device is to be controlled; operating the power output device to supply a voltage to the at least one electrode, thereby to create an electric field in the region of the electrode; passing gas through the electric field, and creating by virtue of the intensity of the electric field a plasma from the gas; and controlling, in accordance with the user input signals to the controller, the power output device to control the power delivered into the plasma. The controller may operate to control the power output device to deliver a predetermined level of energy into the plasma, and the controller may further control the rate of flow of gas through the electric field.

The gas preferably comprises molecules having at least two atoms.

There is also provided a surgical system for use in tissue resurfacing comprising: a user interface which receives input signals from a user relating to desired performance of the system; a power output device which generates a voltage output signal at an output terminal; a gas supply, an instrument having an electrode connected to the output terminal of the power output device thereby to enable the generation of an electric field in the region of the electrode when the power output device is operated to produce an output voltage at the output terminal, the instrument additionally being connected to the gas supply and further comprising a conduit for passing gas from the supply through the electric field in the region of the electrode to create a plasma; and a controller which is connected to the user interface and the power output device, the controller being adapted to receive and process signals from the user interface and to control, on the basis of the user interface signals, the delivery of power from the power output device into the plasma The controller may be additionally adapted to control the time period over which power is delivered into the plasma User interface signals from the user interface to the controller may relate to a total amount of energy to be delivered into the plasma. The system may further comprise a gas flow regulator connected to the controller, the controller being additionally adapted to control to a rate of flow of gas from the supply. The controller may receive feedback signals indicative of power delivered to the plasma.

The power output device may include a tuneable oscillator, and the controller being connected to the oscillator to tune the oscillator on the basis of feedback signals indicative of power attenuated within the instrument. Typically, the output frequency of the oscillator lies within the band of 2400-2500 MHz.

A method is provided for operating a surgical system comprising a power output device which produces an oscillating electrical output signal across a pair of output terminals, an instrument having a pair of electrodes each of which is connected to one of the output terminals of the power output device, a controller which receives input signals from a user interface and controls the power output device accordingly, and a supply of gas connected to the instrument, wherein the method comprises the steps of: operating the power output device to apply an oscillating voltage across the electrodes of the instrument, thereby to create an electric field in the region of the electrodes; passing gas through the electric field and striking a plasma between the electrodes of the instrument; and operating the controller to control the power delivered into the plasma from the power output device.

A surgical system is provided comprising: a power output device which generates a radio frequency oscillating output signal across a pair of output terminals; an instrument having a first pair of electrodes connected to respective output terminals of the power output device and which are part of a first resonant assembly which is resonant at a predetermined frequency, and a second pair of electrodes connected to respective output terminals of the power output device and which are part of a second resonant assembly which is also resonant at the predetermined frequency, a gas supply which supplies gas to the oscillating electric field between the first pair of electrodes and to the oscillating electric field between the second pair of electrodes; wherein the first resonant assembly is resonant at the predetermined frequency prior to formation of a plasma from the gas, and the second resonant assembly is resonant at the predetermined frequency subsequent to the generation of a plasma. In such a system the first pair of electrodes may comprise an inner electrode and an outer electrode extending substantially coaxially with, and around the inner electrode, and the second pair of electrodes may comprise a further inner electrode and said outer electrode. The system may operate such that, during resonance of the first resonant structure, a potential difference is created between the inner electrode and the further inner electrode, and a plasma is initially struck between the inner electrode and the further inner electrode as a result of the potential difference.

A further aspect of the invention includes a surgical system comprising: a power output device which generates a radio frequency oscillating output signal across a pair of output terminals; an instrument having a pair of electrodes connected to respective output terminals of the power output device via a feed structure, to create an oscillating electric field between the electrodes; a gas supply and a conduit from the gas supply to the electric field, to enable gas passing through the electric field to be converted into a plasma and to pass out of an aperture in the instrument; wherein the instrument comprises a voltage transformation assembly providing step up of the voltage output from the power output device, and supplying the stepped-up voltage across the electrodes thereby to intensify the electric field between the electrodes. In such a system the voltage transformation assembly may comprise a structure within the instrument having a resonant frequency within the radio frequency oscillating output bandwidth. The resonant structure may comprise at least one length of transmission line having an electrical length equal to one quarter of a wavelength of the oscillating output signal of the power output device.

Another aspect of the invention provides a surgical instrument comprising: a pair of electrodes; a connector connectible to a feed structure, thereby to enable a signal from a generator to be conveyed to the electrodes; at least a first section of transmission line electrically connected to the electrodes and to the feed structure, the section of transmission line having an electrical length substantially equal to one quarter of a wavelength of an electromagnetic wave having a frequency in the range 2400 MHz to 2500 MHz. This instrument may further comprising a second section of transmission line electrically connected to the connector and to the first section of transmission line, the further section of transmission line having an electrical length substantially equal to the length of the first section of transmission line, wherein the characteristic impedances of the first and second sections of transmission line are different, the first and second sections of transmission line forming an impedance matching assembly between a relatively low characteristic impedance of a feed structure which is connectable to the instrument via the connector and a relatively high impedance electrical load provided by a plasma formed between the electrodes.

There is also provided a surgical instrument comprising: a pair of electrodes separated from each other; a connector for connecting an electrical signal from a feed structure to the electrodes thereby to enable the creation of an electric field between the electrodes; a gas inlet port; a gas conduit for conveying gas from the inlet port to the electrodes thereby to allow gas to pass between the electrodes to enable the creation of a plasma between the electrodes when an electric field is applied between them; and an aperture in the instrument through which plasma may be expelled under pressure of gas passing is along the gas conduit. In such an instrument, gas pressure within the conduit may force plasma out of the aperture in a first direction, and the electrodes may be spaced apart at least in the first direction.

Yet a further aspect includes a surgical instrument comprising: a connector having a pair of electrical terminals; first pair of electrodes provided by an inner electrode and an outer electrode extending coaxially around the inner electrode; a second pair of electrodes provided by a further inner electrode and said outer electrode, the first and second pairs of electrodes being electrically connectable via the connector to a generator to enable creation of an electric field between the inner and outer electrodes and the further inner and outer electrodes respectively, a gas inlet port, and a conduit for conveying gas from the inlet port through the electric field thereby to enable the formation of a plasma from the gas; the first pair of electrodes forming at least a part of a first resonant assembly, and the second pair of electrodes forming at least a part of a second resonant assembly, the first and second resonant assemblies being resonant at a different frequencies prior to the formation of a plasma, thereby to enable, prior to the formation of a plasma, the creation of an electric field between the inner and further inner electrodes which may be used to strike a plasma.

There is also provided a method of operating a surgical instrument having first and second pairs of electrodes, the electrodes of each pair being connected to different output terminals of a power output device which generates an oscillating electrical output signal, the method comprising the steps of: operating the power output device to apply an oscillating electrical signal to the first and second pairs of electrodes; causing resonance of resonant assembly of which the first pair of electrodes form at least a part; creating, by virtue of the resonance, a potential difference and thus an electric field between an electrode of the first pair of electrodes and an electrode of the second pair of electrodes; passing a gas through the electric field and, by virtue of interaction between the electric field and the gas, forming a plasma The electrodes between which the electric field is created may both be connected to the same output terminal of the power output device. Generally, the formation of a plasma results in a change of electrical characteristics of the second pair of electrodes such that they are at least a part of a further resonant assembly which is resonant at the frequency of the oscillating electrical output signal, the method then further comprising the step, subsequent to the formation of a plasma, of causing resonance of the further resonant assembly to create an electric field of sufficient intensity between the second pair of electrodes to maintain the plasma, and delivering power into the plasma from the oscillating output signal.

Yet another aspect of the invention is a method of operating a surgical instrument having first and second pairs of electrodes, the electrodes of each pair being connected to different output terminals of a power output device which generates an oscillating electrical output signal, the method comprising the steps of: operating the power output device to apply an oscillating electrical signal to the first pair of electrodes; applying the oscillating electrical output signal to the first pair of electrodes; causing resonance of a first resonant assembly of which the first pair of electrodes forms a part, and creating an electric field during resonance of the first resonant assembly, passing gas through the electric field, and forming, by virtue of interaction between the electric field and the gas, a plasma; subsequent to the formation of a plasma, applying the oscillating electrical output signal to the second pair of electrodes and causing resonance of a second resonant assembly of which the second pair of electrodes form a part, and maintaining the plasma by delivering into the plasma via the second pair of electrodes, power from the oscillating output signal. The oscillating output signal may remain substantially constant. The first and second pairs of electrodes may be distinct, or they may have an electrode common to both. The electric field is preferably formed between the first pair of electrodes, but may be formed between an electrode of the first pair of electrodes and an electrode of the second pair of electrodes, in which case the electric field may be formed between two electrodes, both of which are connected to the same output terminal of the power output device.

As a result the preferred method, the plasma causes necrosis of living epidermal cells and vaporisation of dead epidermal cells, and where required, produces effects in the dermis.

According to another aspect of the invention, a system for controlling the use of a device for treating human tissue comprises: a generator for providing pulses of energy to the device, the pulses of energy being at selected energy levels; a controller for controlling the supply of energy to the device; an electronic key associated with the device and including memory means; and a read/write device associated with the controller for downloading information from the electronic key and writing information to the memory means; the controller causing the read/write device to send signals to the memory means when energy pulses are provided to the device by the generator to cause updating of a device usage counter in the memory means, whereby the rate at which the counter is incremented increases as the delivered power is increased, the controller further causing the generator to cease the provision of pulses when the device usage counter reaches a predetermined maximum value.

According to another aspect of the invention, there is provided a system for controlling the use of a device for treating human tissue, the system comprising a generator for providing pulses of energy to the device, the pulses of energy being at selected energy levels, a controller for controlling the supply of energy to the device, an electronic key associated with each device and including memory means, and a read/write device associated with the controller for downloading information from the electronic key and writing information to the memory means, the controller causing the read/write device to send a signal to the memory means to update an incremental counter each time a predetermined amount of energy is provided to the device, the controller causing the generator to cease the provision of pulses when the incremental counter reaches a predetermined maximum value, characterised in that the controller updates the incremental counter by a first value for every pulse provided to the device which is below a predetermined threshold energy level, and updates the incremental counter by a second larger value for every pulse provided to the device which is above the predetermined threshold energy level.

According to a further aspect of the invention, a system for controlling the use of a device for treating human tissue comprises: a generator for controlling the use of a device for treating human tissue comprises: a generator for providing pulses of energy to the device, the pulses of energy being at selected energy levels; a controller for controlling the supply of energy to the device; an electronic key associated with the device and including memory means; and a read/write device associated with the controller for downloading information from the electronic key and writing information to the memory means; the controller causing the read/write device to send signals to the memory means when energy pulses are provided to the device by the generator to cause updating of a device usage counter in the memory means whereby the counter is incremented at different rates according to the energy of the pulses so that pulses of a first energy level cause incrementing of the counter more quickly than pulses of a second energy level, the first energy level being higher than the second energy level.

There are a number of electronic key systems on the market, such as the "i-button" system from Dallas Semiconductor Corp. These can be used for a variety of purposes, including personnel access and e-commerce applications. Examples of electronic key systems proposed for use with medical apparatus include U.S. Pat. No. 6,464,689 assigned to Curon Medical and U.S. Pat. No. 5,742,718 assigned to Eclipse Surgical Technologies. Prior art systems such as these can be used to authenticate a disposable handpiece by having the control unit register a unique code carried by the electronic key. These systems can also store usage data for the medical instrument, and patient data for the procedure being undertaken. The present invention provides a simple system, yet one that takes into account that the electronic key may be presented to different control units in an attempt to obtain additional usage time. The system also takes into account that the device may be used at different power settings, and the acceptable usage time may depend upon these power settings.

The preferred system sets a threshold energy level, and increments the counter by a different amount depending on whether the energy supplied is above or below the threshold level. Depending on the memory available, the counter can be incremented every time a pulse is provided to the device, or every time a predetermined amount of energy (i.e. a preset number of pulses) is provided to the device. Conveniently the predetermined threshold energy level is in the range of 0.5 to 2.5 Joules, and typically substantially 2 Joules.

According to a convenient arrangement, the second value (for energy supplied above the threshold) is substantially twice the value of the first value (for energy supplied below the threshold). In one arrangement, the predetermined maximum value is between 500 and 5000 times the first value, typically between 2000 and 3000 times the first value. Thus the system gives up to 5000 pulses at the lower energy levels, or up to 2500 pulses at the higher energy levels.

Alternatively, the controller configuration may be such that the counter is incremented at more than two different rates according to pulse energy, using two or more different energy thresholds. According to another configuration, the rate of incrementing of the counter may increase progressively as the delivered power increases.

Conveniently, the memory means includes a unique identifying code for the electronic key, and /or the controller writes a unique identifying code to the memory means. Additionally, the controller is adapted to cause the read/write device to send a signal to the memory means representative of the time that the electronic key is first presented to the read/write device, or the time that the first pulses of energy are provided to the device. The controller is preferably adapted to compare the current time with the time that the key was presented or the first pulses of energy were provided to the device, and to prevent the provision of pulses when the time difference exceeds a predetermined value. Thus not only can the system confirm the identity of the disposable element presented to the generator, but it can also identify disposable elements that are old in that they were first used prior to a given period of time. Conveniently, the predetermined value is between 6 and 12 hours.

The invention also extends to a method of controlling the use of a device for treating human tissue comprising the steps of providing a controller for controlling the supply of energy to the device, and an electronic key associated with each device, the electronic key including memory means, presenting the electronic key to the controller, reading the value from an incremental counter on the memory means and determining whether it has reached a predetermined maximum value, supplying pulses of energy to the device if the incremental counter has not reached its predetermined maximum value, updating the incremental counter at a rate which increases as the power provided to the device is increased. The increase in the rate of incrementing the counter as the power increases may be brought about by updating the incremental counter by a first value each time that a pulse or a number of pulses is provided to the device below a predetermined threshold energy level, and updating the incremental counter by a second larger value each time that a pulse or a number of pulses is provided to the device above the predetermined threshold energy level.

The invention further resides in a method of skin treatment, comprising the steps of generating pulses of plasma, and, in an initial treatment, applying at least one pulse of plasma at a first energy level to a surface of skin, wherein the application of said at least one pulse of plasma to the surface of skin causes denaturation of collagen within collagen-containing tissue beneath the skin surface without causing the complete removal of epidermis at said surface of skin, and, in a subsequent treatment, applying at least one pulse of plasma at a second energy level to a surface of skin, wherein the application of said at least one pulse of plasma to the surface of skin causes the destruction of the majority of the epidermis.

The initial treatment may be constituted by a single session at which one or more pulses are applied to each area of skin to be treated, or several of such sessions repeated at a time interval ranging from several minutes to a month or more. In the initial treatment, each session results in energy being delivered below that resulting in the destruction of the epidermis.

The subsequent treatment is constituted by a single session, which may involve one or more pulses being applied to each area of skin to be treated. The energy delivered, whether from a single pulse or a series of pulses, is such that the majority of the epidermis is destroyed.

The present invention allows for the control of the energy delivered, whether in single or multiple sessions, such that the useful life of the instrument is maximized without risking the degradation of the instrument. Degradation of the instrument is to be avoided so as to minimize the possibility of variations in the energy being delivered to the skin being treated, and hence the effect the treatment may have on the tissue to be treated.

BRIEF DESCRIPTION OF THE DRAWINGS

Embodiments of the invention will now be described, by way of example and with reference to the accompanying drawings, in which:

FIG. 1 is a schematic drawing illustrating the principle underlying a surgical system for skin resurfacing according to the present invention;

FIG. 2 is a longitudinal cross-section of a surgical instrument for use in a system in accordance with the present invention;

FIG. 3 is a detail of FIG. 2;

FIG. 7 is a schematic drawing of an alternative generator including a magnetron;

FIG. 14 is a section through an embodiment of instrument suitable for use with the generator of FIG. 7;

FIG. 19 is a cut-away perspective view of another alternative instrument; and

FIG. 20 is a longitudinal cross-section of part of the instrument of FIG. 19.

FIG. 21 is a perspective view of an instrument for use in the surgical system of FIG. 1, FIG. 22 is a sectional side view of the instrument of FIG. 21.

DETAILED DESCRIPTION OF PREFERRED EMBODIMENTS

Figure 4:
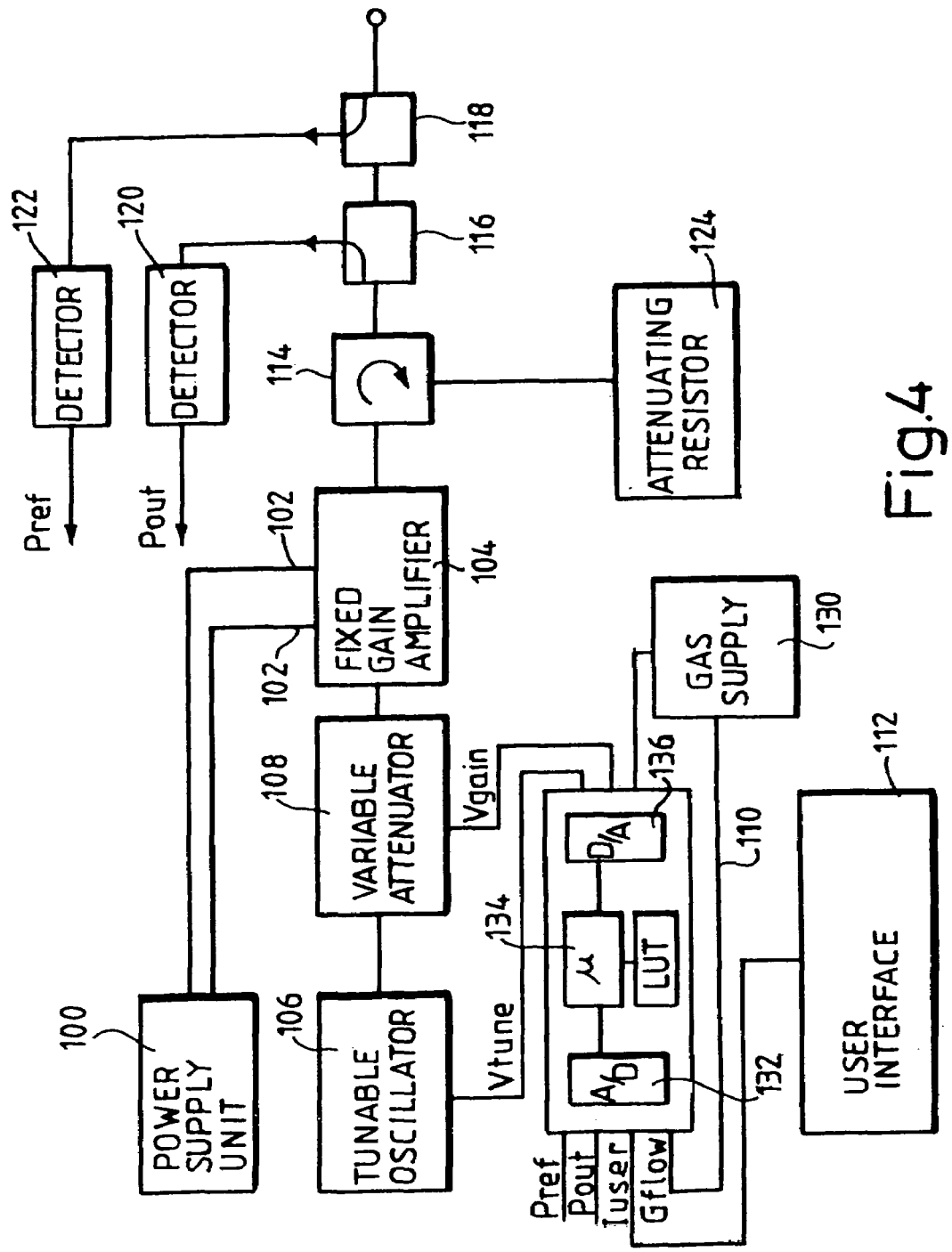
FIG. 4 is a schematic illustration of a generator used in conjunction with the instrument of FIGS. 2 and 3.

Referring to FIG. 1, the principle of operation of embodiments of the invention will now be described. A surgical system comprises a generator 4 which includes a power output 6, typically in the form of an oscillator and an amplifier, or a thermionic power device, and a user interface 8 and a controller 10. The generator produces an output which is coupled via a feed structure including a cable 12 to an electrode 14 of an instrument 16. The system further includes a supply 18 of gas, which is supplied to the instrument by means of a pipe 20. The gas is preferably a gas that enables relatively high energy to be delivered to the tissue per unit energy delivered into the gas at the instrument. Preferably the gas should include a diatomic gas (or gas having more than two atoms), for example, nitrogen, carbon dioxide or air. In use, the generator operates to establish an electric field in the region of the tip 22 of the electrode. Gas from the supply 18 is passed through the electric field. If the field is sufficiently strong, it will have the effect of accelerating free electrons sufficiently to cause collisions with the gas molecules, the result of which is either the dissociation of one or more electrons from the gas molecules to create gaseous ions, or the excitation of electrons in the gas molecules to higher energy states, or dissociation of molecules into constituent atoms, or the excitation of vibrational states in the gaseous molecules. The result in macroscopic terms is the creation of a plasma 24 which is hot. Energy is released from the plasma by way of recombination of electrons and ions to form neutrally charged atoms or molecules and the relaxation to lower energy states from higher energy states. Such energy release includes the emission of electromagnetic radiation, for example, as light, with a spectrum that is characteristic of the gas used. The temperature of the plasma depends upon the nature of the gas and the amount of power delivered to the gas from the electric field (i.e. the amount of energy transferred to a given quantity of gas).

In the preferred embodiment, a low-temperature plasma is formed in nitrogen. This is also known in the art as a Lewis-Rayleigh Afterglow and energy storage by the plasma is dominated by vibrational states of the gaseous molecule and elevated states of electrons still bound to molecules (known as 'metastable states' because of their relatively long lifetime before decay to a lower energy states occurs).

In this condition the plasma will readily react, that is, give energy up due to collision, with other molecules. The plasma emits a characteristic yellow/orange light with a principle wavelength of about 580 nm.

The relatively long-lived states of the plasma is an advantage in that the plasma still contains useful amounts of energy by the time it reaches the tissue to be treated.

The resulting plasma is directed out of an open end of the instrument and towards the tissue of a patient, to cause modification or partial or total removal thereof.

Upon impact, the nitrogen plasma penetrates a short distance into the tissue and rapidly decays into a low energy state to reach equilibrium with its surroundings. Energy is transferred through collisions (thus heating the tissue) and emission of electromagnetic energy with a spectrum typically extending from 250 to 2500 nm. The electromagnetic energy is absorbed by the tissue with consequent heating.

Where the system is employed for the purpose of skin resurfacing, there are a variety of skin resurfacing effects which may be achieved by the application of a plasma to the skin, and different effects are achieved by delivering different amounts of energy to the skin for different periods of time. The system operates by generating a plasma in short pulses. The various combinations of these parameters result in different skin resurfacing effects. For example, applying relatively high power in extremely short pulses (i.e. over an extremely short period of time) will result in the virtual instantaneous vaporisation of an uppermost layer of the epidermis (i.e. dissociation into tiny fragments, which in this situation are usually airborne). The high power delivery results in the vaporisation of the tissue, while the short time period over which energy is delivered prevents deeper penetration of thermally induced tissue damage. To deliver high power levels to the tissue, a high temperature plasma is required, and this can be obtained by delivering energy at a high level into a given quantity of gas (i.e. high energy over a short period of time, or high power) from the electric field. It should be noted that the temperature of the plasma decreases with increasing distance from the electrode tip, which means that the stand-off distance of the instrument from the surface of the skin will affect the temperature of the plasma incident upon the skin and, therefore, the energy delivered to the skin over a given time period. This is a relatively superficial skin resurfacing treatment, but has the advantage of extremely short healing times.

A deeper effect, caused by thermal modification and eventual removal of a greater thickness of tissue, may be obtained by delivering lower levels of power to the skin but for longer periods of time. A lower power level and, thus, a lower rate of energy delivery avoids substantially instantaneous vaporisation of tissue, but the longer period over which power is delivered results in a greater net energy delivery to the tissue and deeper thermal effects in the tissue. The resultant blistering of the skin and subsequent tissue necrosis occur over a substantially longer period of time than in the case of a superficial treatment. The most deeply penetrative skin resurfacing, which may involve an stepwise process whereby several "passes" are made over the tissue so that a given area of skin is exposed to the plasma on two or more occasions, can penetrate sufficiently deeply to cause the denaturing of collagen in the dermis. This has applicability in the removal or remodelling of scar tissue (such as that caused by acne, for example), and reduction of wrinkles. Depilation of the skin surface may also be achieved.

The system and methods of the present invention may also be used to debride wounds or ulcers, or in the treatment of a variety of cutaneous or dermatological disorders. including: malignant tumours (whether primarily or secondarily involving the skin); port wine stains; telangiectasia; granulomas; adenomas; haemangioma; pigmented lesions; nevi; hyperplastic, proliferative and inflammatory fibrous papules; rhinophyma; seborrhoeic heratoses; lymphocytoma; angiofibromata; warts; neurofibromas; condylomata; keliod or hypertrophic scar tissue.

The system and methods of the present invention also have applicability to numerous other disorders, and in this regard the ability to vary the depth of tissue effect in a very controlled manner is particularly advantageous. For example, in a superficial mode of treatment, tissue surfaces of the body other than skin may be treated, including the linings of the oropharynx, respiratory and gastrointestinal tracts in which it is desirable to remove surface lesions, such as leudoplakia (a superficial pre-cancerous lesion often found in the oropharynx), while minimising damage to underlying structures. In addition, the peritoneal surface of organs and structures within the abdomen may be a site for abnormal implantation of endometrial tissue derived from the uterus. These are often constituted by superficial plaques which may also be treated using the invention set in a superficial mode of treatment. If such lesions involve deeper layers of tissue then these may be treated by multiple applications using the invention or the depth of tissue effect may be adjusted using the control features included within the invention and which are further described herein.

By employing a system or method in accordance with the invention with a setting designed to achieve a deeper effect, tissue structures deep to the surface layer may be treated or modified. Such modification may include the contraction of collagen containing tissue often found in tissue layers deep to the surface layer. The depth control of the system allows vital structures to be treated without, for instance, causing perforation of the structure. Such structures may include parts of the intestine where it is desirable to reduce their volume, such as in gastroplexy (reducing the volume of the stomach), or in instances where the intestine includes abnormal out-pouchings or diverticular. Such structures may also include blood vessels which have become abnormally distended by an aneurysm or varicosities, common sites being the aortic artery, the vessels of the brain or in the superficial veins of the leg. Apart from these vital structures, musculoskeletal structures may also be modified where they have become stretched or lax. A hiatus hernia occurs when a portion of the stomach passes through the crura of the diaphragm which could, for example, be modified using the instrument such that the aperture for the stomach to pass through is narrowed to a point at which this does not occur by contracting the crura. Hernias in other areas of the body may be similarly treated including by modifying collagen-containing structures surrounding the weakness through which the herniation occurs. Such hernias include but are not limited to inguinal and other abdominal hernias.

Various embodiments of system for tissue resurfacing will now be described in further detail. Referring to FIGS. 2 and 3, a skin resurfacing instrument 16 has an outer shaft 30 with has a connector 26 at its proximal end, by means of which the instrument may be connected to the output terminals of a generator (described in more detail with reference to FIG. 4), usually via a flexible cable, as shown in FIG. 1. The instrument also receives a supply of nitrogen at inlet port 32, which is fed initially along an annular conduit 34 formed between shaft 30 and a length of coaxial feed cable 40, and subsequently, via apertures 36 along a further sections of annular conduit 38A and 38B. The sections 38A, 38B of annular conduit are formed between a conductive sleeve 50, which is connected to the outer conductor 44 of the coaxial feed cable, and conductive elements 52 and 54 respectively which are connected to the inner conductor 42 of the coaxial feed cable 40. At the distal end of the annular conduit 38B the gas is converted into a plasma under the influence of an oscillating high intensity electric field E between an inner needle-like electrode 60 provided by the distal end of the conductive element 54, and an outer second electrode 70 provided by a part of the sleeve 50 which is adjacent and coextensive with the needle electrode 60. The resultant plasma 72 passes out of an aperture 80 formed in a ceramic disc 82 in the distal end of the instrument largely under the influence of the pressure from the nitrogen supply, the insulating nature of the disc 82 serving to reduce or avoid preferential arcing between the electrodes 60 and 70.

The inner electrode 60 is connected to one of the generator output terminals via the conductive elements 52, 54 and the inner conductor 42 of the coaxial feed structure, and the outer electrode 70 is connected to the other generator output terminal via the conductive sleeve 50 and the outer conductor 44 of the coaxial feed structure 40. (Waveguides may also be used as the feed structure.) The intensity of the electric field between them therefore, oscillates at the output frequency of the generator, which in this embodiment is in the region of 2450 MHz. In order to generate a plasma from the nitrogen gas, a high intensity electric field is required. In this regard the relatively pointed configuration of the needle electrode 60 assists in the creation of such a field, because charge accumulates in the region of the tip, which has the effect of increasing the field intensity in that region. However, the creation of a high intensity electric field requires a large potential difference between the inner and outer electrodes 60, 70 and, generally speaking, the magnitude of the potential difference required to create such a field increases with increasing separation of the electrodes. The electric field intensity required to strike a plasma from nitrogen (and thus create a plasma) is in the region of 3 M.Newtons per Coulomb of charge, which translated into a uniform potential difference, equates roughly to a potential difference of 3 kV between conductors separated by a distance of 1 mm. In the instrument illustrated in FIG. 2, the separation between the inner and outer electrodes 60, 70 is approximately 3 mm, so that were the field uniform the voltage required to achieve the requisite field intensity would be approximately 10 kV. However the geometry of the electrode 60 is such as to concentrate charge in regions of conductor which have a small curvature thereby intensifying the electric field regions adjacent such conductors and reducing the magnitude of potential difference which must be supplied to the electrodes in order to create a field of the required strength. Nonetheless, in practice it is not necessarily desirable to supply a potential difference of sufficient magnitude to the electrodes 60, 70 directly from the generator, because the insulator of the feed structure used to connect the generator output to the electrodes 60, 70 may be subject to breakdown.

In the embodiment described above with reference to FIGS. 1 to 3, the output voltage of the generator is preferably of the order of 100V. In order to obtain a high enough voltage across the electrodes 60, 70 to strike a plasma, therefore, it is necessary to provide a step-up, or upward transformation of the supply voltage from the generator. One way of achieving this is to create a resonant structure which incorporates the electrodes 60, 70. If an output signal from the generator is supplied to the resonant structure (and, therefore, the electrodes) at a frequency which is equal to or similar to its resonant frequency, the resulting resonance provides voltage multiplication of the generator output signal across the electrodes 60, 70 the magnitude of which is determined by the geometry of the structure, the materials used within the structure (e.g. the dielectric materials), and the impedance of a load. In this instrument, the resonant structure is provided by a combination of two impedance matching structures 92, 94 the function and operation of which will be described in more detail subsequently.

The use of a resonant structure is one way of providing a sufficiently high voltage across the electrodes 60, 70 to strike a plasma. For the instrument to be effective, however, it is necessary for the generator to deliver a predetermined and controllable level of power to the plasma, since this affects the extent to which the nitrogen is converted into plasma, which in turn affects the energy which may be delivered to the tissue in the form of heat. In addition it is desirable to have efficient transmission of power from the generator to the load provided by the plasma. As mentioned above, the output frequency of the generator in the present example is in the ultra high frequency (UHF) band of frequencies, and lies in the region of 2450 MHz, this being a frequency whose use is permitted for surgical purposes by ISM legislation. At frequencies of this magnitude is appropriate to consider the transmission of electrical signals in the context of such a surgical system as the transmission of electromagnetic waves, and the feed structures for their efficient propagation of taking the form of coaxial or waveguide transmission lines.

In the instrument of FIG. 2, the coaxial cable 40 provides the transmission line feed structure from the generator 4 to the instrument 16. The inner and outer conductors 42, 44 of the coaxial feed structure 40 are spaced from each other by an annular dielectric 46. To provide efficient transmission of power from the output of the generator using a transmission line, the internal impedance of the generator is desirably equal to the characteristic impedance of the transmission line. In the present example the internal impedance of the generator is 50 ohms, and the characteristic impedance of the coaxial cable 40 is also 50 ohms. The load provided to the generator prior to striking plasma is of the order of 5k ohms. Owing to this large difference in impedance between the generator impedance and feed structure on the one hand, and the load on the other, delivering power to the load directly from the feed structure will result in substantial losses of power (i.e. power output from the generator which is not delivered to the load) due to reflections of the electromagnetic waves at the interface between the feed structure and the load. Thus, it is not preferable simply to connect the inner and outer conductors 42, 44 of the coaxial cable 40 to the electrodes 60, 70 because of the resultant losses. To mitigate against such losses it is necessary to match the relatively low characteristic impedance of the cable 40 and the relatively high load impedance, and in the present embodiment this is achieved by connecting the load to the feed structure (whose characteristic impedance is equal to that of the generator impedance) via an impedance transformer provided by two sections 92, 94 of transmission line having different characteristic impedances to provide a transition between the low characteristic impedance of the coaxial feed structure and the high impedance load. The matching structure 92 has an inner conductor provided by the conductive element 52, which has a relatively large diameter, and is spaced from an outer conductor provided by the conductive sleeve 50 by means of two dielectric spacers 56. As can be seen from FIG. 2, the spacing between the inner and outer conductors 52, 50 is relatively small, as a result of which the matching structure 92 has a relatively low characteristic impedance (in the region of 8 ohms in this embodiment). The matching structure 94 has an inner conductor provided by the conductive element 54, and an outer conductor provided by the sleeve 50. The inner conductor provided by the conductive element 54 has a significantly smaller diameter than conductive element 52, and the relatively large gap between the inner and outer conductors 50, 54 results in a relatively high characteristic impedance (80 ohms) of the matching structure 94.

Electrically, and when operational, the instrument may be thought of as four sections of different impedances connected in series: the impedance $Z_F$ of the feed structure provided by the coaxial cable 40, the impedance of the transition structure provided by the two series connected matching structures 92, 94 of transmission line, having impedances $Z_{92}$ and $Z_{94}$ respectively, and the impedance $Z_L$ of the load provided by the plasma which forms in the region of the needle electrode 60. Where each of the sections 92, 94 of the matching structure has an electrical length equal to one quarter wavelength at 2450 MHz, the following relationship between impedances applies when the impedance of the load and the feed structure are matched:

$$Z_L/Z_F = Z_{94}^2/Z_{92}^2$$

The impedance $Z_L$ of the load provided to the generator by the plasma is in the region of 5k ohms; the characteristic impedance $Z_F$ of the coaxial cable 40 is 50 ohms, meaning that the ratio $Z_{94}^2/Z_{92}^2 = 100$ and so $Z_{94}/Z_{92}=10$. Practical values have been found to be 80 ohms for $Z_{94}$, the impedance of the matching structure section 94, and 8 ohms for $Z_{92}$, the impedance of matching structure section 92.

The requirement that each of the matching structures 92, 94 are one quarter wavelength long is an inherent part of the matching process. Its significance lies in that at each of the interfaces between different characteristic impedances there will be reflections of the electromagnetic waves. By making the sections 92, 94 one quarter wavelength long, the reflections at e.g. the interface between the coaxial feed structure 40 and the section 92 will be in anti phase with the reflections at the interface between the section 92 and the section 94, and so will destructively interfere; the same applies to the reflections at the interfaces between the sections 92 and 94 on the one hand and the reflections at the interface between section 94 and the load on the other. The destructive interference has the effect of minimising power losses due to reflected waves at interfaces between differing impedances, provided that the net reflections of the electromagnetic waves having nominal phase angle of 0 radians are of equal intensity to the net reflections having a nominal phase angle of π radians (a condition which is satisfied by selecting appropriate impedance values for the different sections 92, 94).

Referring now to FIG. 4, an embodiment of generator used in conjunction with the embodiment of instrument described above comprises a power supply unit 100, which receives an alternating current mains input and produces a constant DC voltage across a pair of output terminals 102, which are connected to a fixed gain solid state power amplifier 104. The power amplifier 104 receives an input signal from a tunable oscillator 106 via a variable attenuator 108. The power amplifier 104, tunable oscillator 106, and variable attenuator 108 may be thought of as an AC power output device. Control of the frequency of oscillation of the oscillator, and the attenuator 108 is performed by means of voltage outputs $V_{tune}$ and $V_{gain}$ from a controller 110 (the operation of which will subsequently be described in more detail) in dependence upon feedback signals, and input signals from a user interface 112. The output of the amplifier 104 passes through a circulator 114, and then sequentially through output and return directional couplers 116,118 which in conjunction with detectors 120,122 provide an indication of the power output $P_{out}$ by the generator and the power reflected Pref back into the generator respectively. Power reflected back into the generator passes through the circulator 114 which directs the reflected power into an attenuating resistor 124, whose impedance is chosen so that it provides a good match with the feed structure 40 (i.e. 50 ohms). The attenuating resistor has the function of dissipating the reflected power, and does this by converting the reflected power into heat.

Figure 5:
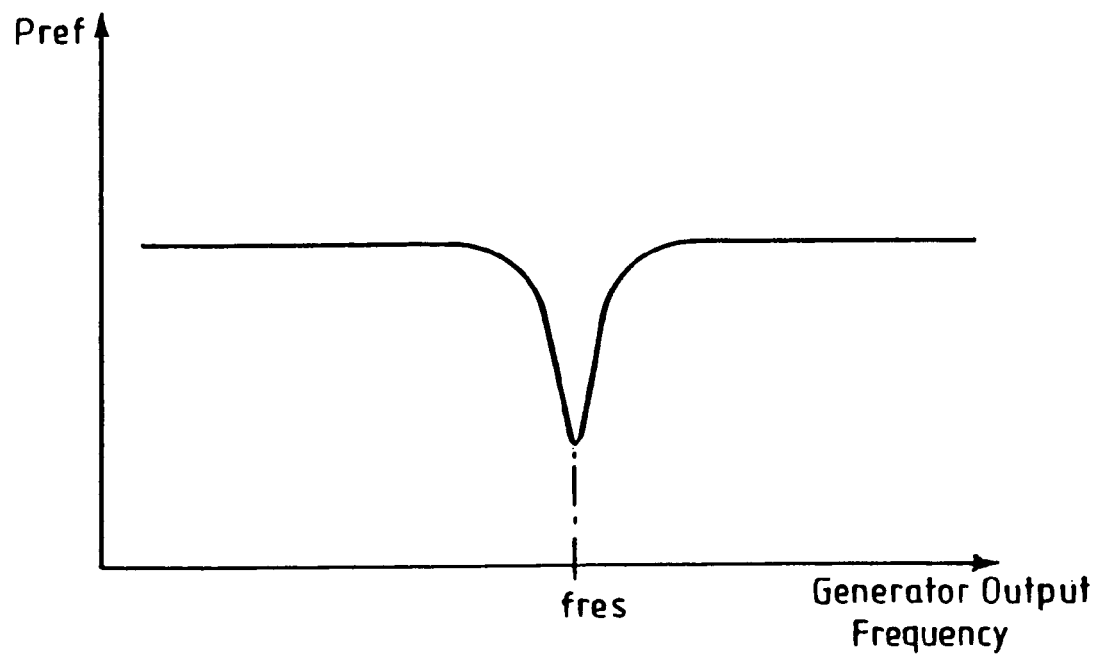
FIG. 5 is a graph showing reflected power as a function of operating frequency.

The controller 110 receives input signals $I_{user}$, $P_{out}$, $P_{Ref}$, $G_{flow}$ from the user interface, the output and reflected power detectors 120,122 and a gas flow regulator 130, respectively, the latter controlling the rate of delivery of nitrogen. Each of the input signals passes through an analogue to digital converter 132 and into a microprocessor 134. The microprocessor 134 operates, via a digital to analogue converter 136 to control the value of three output control parameters: $V_{tune}$ which controls the tuning output frequency of the oscillator 106; $V_{gain}$ which controls the extent of attenuation within the variable attenuator 108 and therefore effectively the gain of the amplifier 104; and $G_{flow}$ the rate of flow of gas through the instrument, with the aim of optimising the performance of the system. This optimisation includes tuning the output of the oscillator 106 to the most efficient frequency of operation, i.e. the frequency at which most power is transferred into the plasma. The oscillator 106 may generate output signals throughout the ISM bandwidth of 2400-2500 MHz. To achieve optimisation of the operating frequency, upon switch-on of the system, the microprocessor 134 adjusts the $V_{gain}$, output to cause the attenuator to reduce the generator output power to an extremely low level, and sweeps the frequency adjusting voltage output $V_{tune}$ from its lowest to its highest level, causing the oscillator to sweep correspondingly through its 100 MHz output bandwidth. Values of reflected power $P_{ref}$ are recorded by the microprocessor 134 throughout the bandwidth of the oscillator, and FIG. 5 illustrates a typical relationship between output frequency of the generator and reflected power $P_{ref}$. It can be seen from FIG. 5 that the lowest level of reflected power occurs at a frequency $f_{ref}$ which corresponds to the resonant frequency of the resonant structure within the instrument 16. Having determined from an initial low power frequency sweep the value of the most efficient frequency at which power may be delivered to the electrode, the microprocessor then tunes the oscillator output frequency to the frequency fres. In a modification, the controller is operable via a demand signal from the user interface (the demand signal being by a user via the user interface) to perform an initial frequency sweep prior to connection of the instrument 16 to the generator. This enables the controller to map the feed structure between the power output device and the instrument to take account of the effect of any mismatches between discrete sections of the feed structure etc., which have an effect upon the attenuation of power at various frequencies. This frequency mapping may then be used by the controller 110 to ensure that it takes account only of variations in the attenuation of power with frequency which are not endemically present as a result of components of the generator and/or feed structure between the generator and the instrument.

The operational power output of the power output device is set in accordance with the input signal $I_{user}$ to the controller 110 from the user interface 112, and which represents a level of demanded power set in the user interface 112 by an operator. The various possible control modes of the generator depend upon the user interface 112, and more particularly the options which the user interface is programmed to give to a user. For example, as mentioned above, there are a number of parameters which may be adjusted to achieve different tissue effects, such as power level, gas flow rate, the length of the time period (the treatment pulse width) for which the instrument is operational to generate plasma over a particular region of the skin, and the stand-off distance between the aperture at the distal end of the instrument 16 and the tissue. The user interface 112 offers the user a number of alternative control modes each of which will allow the user to control the system in accordance with differing demand criteria For example, a preferred mode of operation is one which mimics the operational control of laser resurfacing apparatus, since this has the advantage of being readily understood by those currently practising in the field of skin resurfacing. In the laser resurfacing mode of operation, the user interface invites a user to select a level of energy delivery per surface area (known in the art as "fluence") per pulse of the instrument. When operating in this mode, the microprocessor sets $V_{gain}$ so that the power output device has a pre-set constant output power, typically in the region of 160 W, and the input signal $I_{user}$ from the user is converted into a demanded time period represented by the pulse width, calculated from the required energy per treatment pulse and the constant level of output power. However, the voltage signal $V_{gain}$ is also used to switch the generator output on and off in accordance with input signals $I_{user}$ from the user interface. Thus, for example, when the user presses a button on the handle of the instrument (not shown), a signal sent by the user interface 112 to the microprocessor 134, which then operates to produce a pulse of predetermined width (e.g. 20 ms) by altering $V_{gain}$ from its quiescent setting, at which the attenuator output 108 is such that there is virtually no signal for the amplifier 104 to amplify, and the generator output is negligible, to a value corresponding to the pre-set constant output power for a period of time equal to the demanded pulse width. This will have the effect of altering the amplifier output from its quiescent level to the pre-set constant output power level for a time period equal to the demanded pulse width, and ultimately of creating a plasma for such a time period. By altering the pulse width according to user input, pulses of selected energies can be delivered, typically, in the range of from 6 ms to 20 ms. These pulses can be delivered on a "one-shot" basis or as a continuous train of pulses at a predetermined pulse frequency.

The surface area over which the energy is delivered will typically be a function of the geometry of the instrument, and this may be entered into the user interface in a number of ways. In one embodiment the user interface stores surface area data for each different geometry of instrument that may be used with the generator, and the instrument in operation is either identified manually by the user in response to a prompt by the user interface 112, or is identified automatically by virtue of an identification artefact on the instrument which is detectable by the controller (which may require a connection between the controller and the instrument). Additionally the surface area will also be a function of the stand-off distance of the instrument aperture 82 from the tissue, since the greater the stand-off the cooler the plasma will be by the time it reaches the surface, and also, depending on the instrument geometry, the instrument may produce a divergent beam. Instruments may be operated with a fixed stand-off distance, for example by virtue of a spacer connected to the distal end of the instrument, in which case the surface area data held within the user interface will automatically take account of the stand-off distance. Alternatively the instruments may be operated with a variable stand-off distance, in which case the stand-off distance must be measured, and fed back to the controller to enable it to be taken into account in the surface area calculation.

A further parameter which can affect the energy per unit area is the gas flow rate, and in one preferred embodiment the controller preferably contains a look-up table 140 of flow rate $G_{flow}$ against generator output power $P_{out}$ for a variety of constant output power levels, and the flow rate for a given output power level is adjusted accordingly. In a further modification the gas flow rate may be adjusted dynamically to take account of variations in stand-off distance, for example, and is preferably switched off between pulses.

As described above, for optimum ease of use in the resurfacing mode, the power output device will ideally deliver a constant output power over the entire duration of an output, since this facilitates easy control of the total energy output in a given pulse. With a constant power output, the controller is able to control the total energy delivered per pulse simply switching the power output device on (by the means of the signal $V_{gain}$) for a predetermined period of time, calculated on the basis of the output power level. It may, however, in practice be the case that the power output varies to a significant extent with regard to the accuracy to within which it is required to determine to the total energy delivered per output pulse. In this case the microprocessor is programmed to monitor the output power by integrating $P_{out}$ (from detector 120) with respect to time, and switching the power output device off by altering $V_{gain}$ to return the variable attenuator 108 to its quiescent setting.

A further complication in the control of the operation of the system arises in that the creation of a plasma at aperture 80 amounts in simplistic electrical terms to extending the length of the needle electrode 60, since the plasma is made up of ionised molecules, and is therefore conductive. This has the effect of lowering the resonant frequency of the resonant structure, so that the optimum generator output at which power may be delivered to the instrument for the purpose of striking a plasma is different to the optimum frequency at which power may be delivered into an existent plasma. To deal with this difficulty, the microprocessor 134 is programmed continuously to tune the oscillator output during operation of the system. In one preferred mode the technique of "dither" is employed, whereby the microprocessor 134 causes the oscillator output momentarily to generate outputs at frequencies 4 MHz below and above the current output frequency, and then samples, via the reflected power detector 122 the attenuation of power at those frequencies. In the event that more power is attenuated at one of those frequencies than at the current frequency of operation, the microprocessor re-tunes the oscillator output to that frequency at which greater power attenuation occurred, and then repeats the process. In a further preferred mode of operation, the microprocessor 134 records the magnitude of the shift in resonant frequency when a plasma is struck, and in subsequent pulses, shifts the frequency of the oscillator 106 correspondingly when the system goes out of tune (i.e. when a plasma is struck), whereupon the technique of dither is then employed. This has the advantage of providing a more rapid re-tuning of the system once a plasma is first struck.

As mentioned above, in the embodiment shown in FIG. 4, the amplifier 104 is typically set to produce around 160 W of output power. However, not all of this is delivered into the plasma Typically power is also lost through radiation from the end of the instrument in the form of electromagnetic waves, from reflection at connections between cables, and in the form of dielectric and conductive losses (i.e. the attenuation of power within the dielectrics which form part of the transmission line). In the instrument design of FIGS. 2 and 3 it is possible to take advantage of dielectric loss by virtue of feeding the gas through the annular conduits 38A,B of the sections 92, 94 of the impedance matching structure; in this way, dielectric power losses into the gas serve to heat up the gas, making it more susceptible to conversion into a plasma Referring now to FIG. 6, in a modification of the instrument 14 shown in FIGS. 2 and 3, an end cap 84, made of conducting material, is added to the distal end of the instrument 14. The end cap is electrically connected to the sleeve 50 and is, therefore, part of the electrode 70. The provision of the end cap 84 has several beneficial effects. Firstly, since the electric field preferentially extends from conductor to conductor, and the end cap 84 effectively brings the electrode 70 closer to the tip of the needle electrode 60, it is believed that its geometry serves to increase the intensity of the electric field in the region through which the plasma passes as it is expelled from the instrument, thereby accelerating ions within the plasma. Secondly, the physical effect of the end cap 84 on the plasma is that of directing the plasma in a more controlled manner. Thirdly the outer sheath currents on the instrument (i.e. the current travelling up the outside of the instrument back towards the generator) are reduced significantly with the end cap 84, since the electrode 60, even when electrically extended by a plasma, extends to a lesser extent beyond the end of the instrument, and so losses of this nature are reduced.

In an alternative, and simpler embodiment of system operating at an output frequency in the range of 2450 MHz, a power output device capable of delivering significantly more power than a solid state amplifier may be employed. With increased available power from the power output device, the required voltage step-up is lower and so the role played by resonant structures (for example) decreases.

Accordingly, and referring now to FIG. 7, an alternative generator has a high voltage rectified AC supply 200 connected to a thermionic radio frequency power device, in this case to a magnetron 204. The magnetron 204 contains a filament heater (not shown) attached to the magnetron cathode 204C which acts to release electrons from the cathode 204C, and which is controlled by a filament power supply 206; the greater the power supplied to the filament heater, the hotter the cathode 204C becomes and therefore the greater the number of electrons supplied to the interior of the magnetron. The magnetron may have a permanent magnet to create a magnetic field in the cavity surrounding the cathode, but in this embodiment it has an electromagnet with a number of coils (not shown) which are supplied with current from an electromagnet power supply 208. The magnetron anode 204A has a series of resonant chambers 210 arranged in a circular array around the cathode 204C and its associated annular cavity. Free electrons from the cathode 204C are accelerated radially toward the anode 204A under the influence of the electric field created at the cathode 204C by the high voltage supply 200. The magnetic field from the electromagnet (not shown) accelerates the electrons in a direction perpendicular to that of the electric field, as a result of which the electrons execute a curved path from the cathode 204C towards the anode 204A where they give up their energy to one of the resonant chambers 210. Power is taken from the resonant chambers 210 by a suitable coupling structure to the output terminal The operation of magnetron power output devices is well understood per se and will not be described further herein. As with the generator of FIG. 4, a circulator (not shown in FIG. 7) and directional couplers may be provided.

The magnetron-type power output device is capable of generating substantially more power than the solid state power output device of FIG. 4, but is more difficult to control. In general terms, the output power of the magnetron increases: (a) as the number of electrons passing from the cathode to the anode increases; (b) with increased supply voltage to the cathode (within a relatively narrow voltage band); (c) and with increased magnetic field within the magnetron. The high voltage supply 200, the filament supply 206 and the electromagnetic supply 208 are, therefore, all controlled from the controller in accordance with input settings from the user interface, as in the case of the solid state amplifier power output device. Since the magnetron is more difficult to control, it is less straightforward to obtain a uniform power output over the entire duration of a treatment pulse (pulse of output power). In one method of control, therefore, the controller operates by integrating the output power with respect to time and turning the high voltage supply 200 off (thus shutting the magnetron off) when the required level of energy has been delivered, as described above. Alternatively, the output of the cathode supply may be monitored and controlled to provide control of output power by controlling the current supplied, the cathode/anode current being proportional to output power.

A further alternative generator for use in a system in accordance with the invention, and employing a magnetron as the power output device, will now be described with reference to FIG. 8. As in the embodiment of FIG. 7, power for the magnetron 204 is supplied in two ways, firstly as a high DC voltage 200P for the cathode and as a filament supply 206P for the cathode heater. These power inputs are both derived, in this embodiment, from a power supply unit 210 having a mains voltage input 211. A first output from the unit 210 is an intermediate level DC output 210P in the region of 200 to 400V DC (specifically 350V DC in this case) which is fed to a DC converter in the form of a inverter unit 200 which multiplies the intermediate voltage to a level in excess of 2 kV DC, in this case in the region of 4kV.

The filament supply 206 is also powered from the power supply unit 210. Both the high voltage supply represented by the inverter unit 200 and the filament supply 206 are coupled to a CPU controller 110 for controlling the power output of the magnetron 204 in a manner which will be described hereinafter.

A user interface 112 is coupled to the controller 110 for the purpose of setting the power output mode, amongst other functions.

The magnetron 204 operates in the UHF band, typically at 2.475 GHz, producing an output on output line 204L which feeds a feed transition stage 213 converting the waveguide magnetron output to a coaxial 50 ohms feeder, low frequency AC isolation also being provided by this stage. Thereafter, circulator 114 provides a constant 50 ohms load impedance for the output of the feed transition stage 213. Apart from a first port coupled to the transition stage 213, the circulator 114 has a second port 114A coupled to a UHF isolation stage 214 and hence to the output terminal 216 of the generator. A third port 114B of the circulator 114 passes power reflected back from the generator output 216 via port 114A to a resistive reflected power dump 124. Forward and reflected power sensing connections 116 and 118 are, in this embodiment, associated with the first and third circulator ports 114A and 114B respectively, to provide sensing signals for the controller 110.

The controller 110 also applies via line 218 a control signal for opening and closing a gas supply valve 220 so that nitrogen gas is supplied from source 130 to a gas supply outlet 222. A surgical instrument (not shown in FIG. 8) connected to the generator has a low-loss coaxial feeder cable for connection to UHF output 216 and a supply pipe for connection to the gas supply outlet 222.

It is important that the effect produced on tissue is both controllable and consistent, which means that the energy delivered to the skin should be controllable and consistent during treatment. For treatment of skin or other surface tissue it is possible for apparatus in accordance with the invention to allow a controlled amount of energy to be delivered to a small region at a time, typically a circular region with a diameter of about 6 mm. As mentioned above, to avoid unwanted thermal affects to a depth greater than required, it is preferred that relatively high powered plasma delivery is used, but pulsed for rapid treatment to a limited depth. Once a small region is treated, typically with a single burst of radio frequency energy less than 100 ms in duration (a single "treatment pulse"), the user can move the instrument to the next treatment region before applying energy again. Alternatively, plural pulses can be delivered at a predetermined rate. Predictability and consistency of affect can be achieved if the energy delivered to the tissue per pulse is controlled and consistent for a given control setting at the user interface. For this reason, the preferred generator produces a known power output and switches the radio frequency power on and off accurately. Generally, the treatment pulses are much shorter than 100 ms, e.g. less than 30 ms duration, and can be as short as 2 ms. When repeated, the repetition rate is typically in the range of from 0.5 or 1 to 10 or 15 Hz.

The prime application for magnetron devices is for dielectric heating. Power control occurs by averaging over time and, commonly, the device is operated in a discontinuous mode at mains frequency (50 or 60 Hz). A mains drive switching circuit is applied to the primary winding of the step-up transformer, the secondary winding of which is applied to the magnetron anode and cathode terminals. Commonly, in addition, the filament power supply is taken from an auxiliary secondary winding of the step-up transformer. This brings the penalty that the transient responses of the heater and anode-cathode loads are different; the heater may have a warm-up time of ten to thirty seconds whereas the anode-cathode response is less than 10 µs, bringing unpredictable power output levels after a significant break. Due to the discontinuous power feed at mains frequency, the peak power delivery may be three to six times the average power delivery, depending on the current smoothing elements in the power supply. It will be appreciated from the points made above that such operation of a magnetron is inappropriate for tissue resurfacing. The power supply unit of the preferred generator in accordance with the present invention provides a continuous power feed for the radio frequency power device (i.e. the magnetron in this case) which is interrupted only by the applications of the treatment pulses. In practice, the treatment pulses are injected into a power supply stage which has a continuous DC supply of, e.g., at least 200V. The UHF circulator coupled to the magnetron output adds to stability by providing a constant impedance load.

Figure 8:
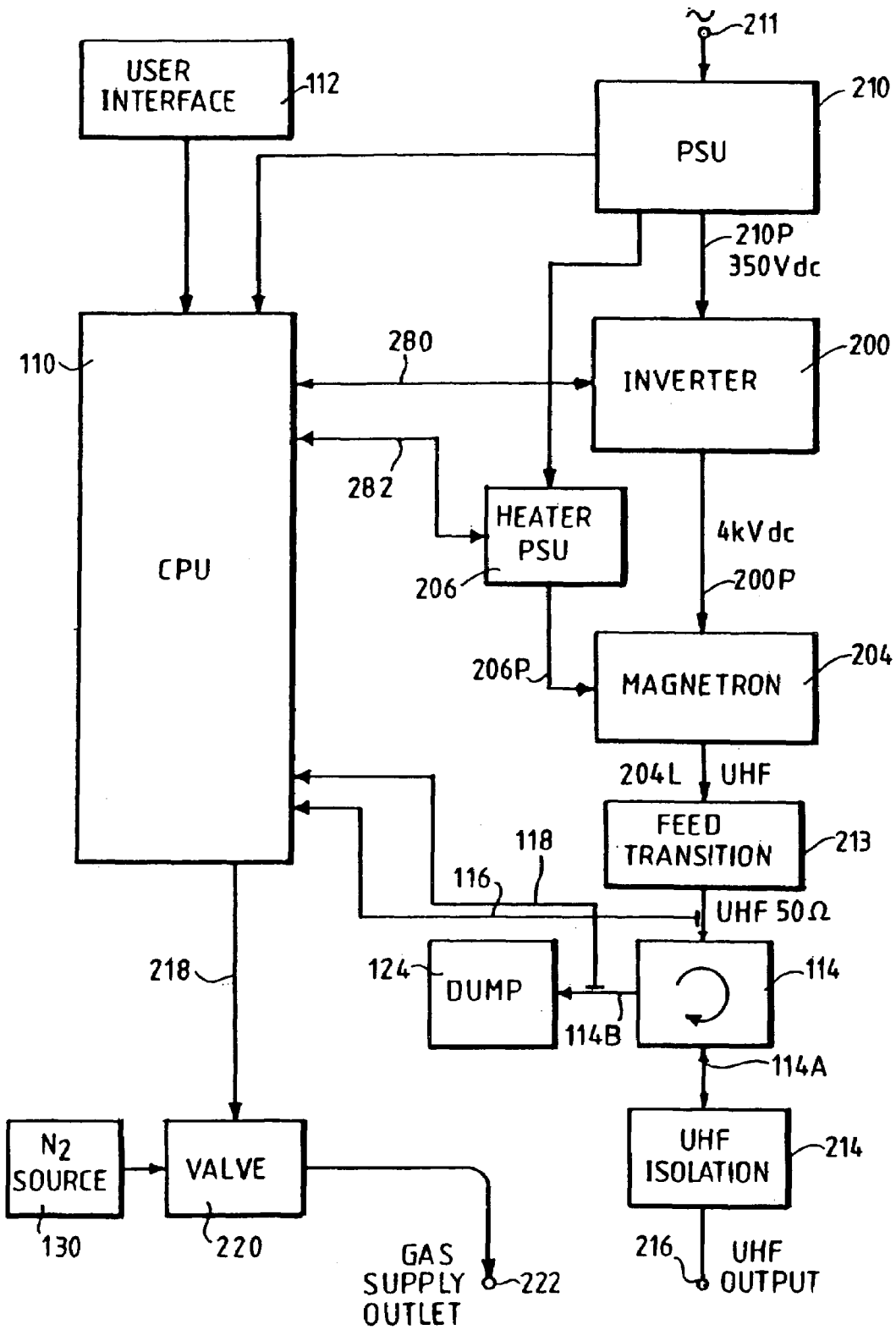
FIG. 8 is a more detailed block diagram of a generator including a magnetron.

In the generator illustrated in FIG. 8, the desired controllability and consistency of effect is achieved, firstly, by use of an independent filament supply. The controller 110 is operated to energise the magnetron heater which is then allowed to reach a steady state before actuation of the high voltage supply to the magnetron cathode.

Figure 9:
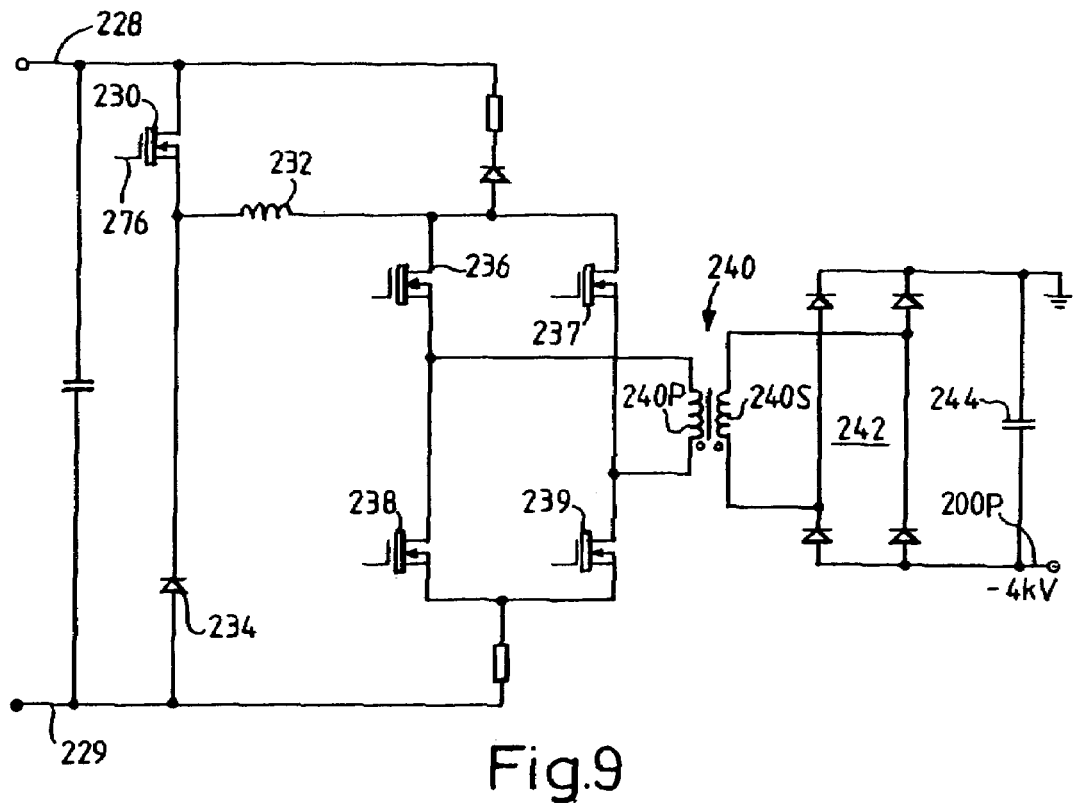
FIG. 9 is a circuit diagram of an inverter unit of the generator of FIG. 8.

Secondly, the high voltage power supply chain avoids reliance on heavy filtering and forms part of a magnetron current control loop having a much faster response than control circuits using large shunt filter capacitances. In particular, the power supply chain includes, as explained above with reference to FIG. 8, an inverter unit providing a continuous controllable current source applied at high voltage to the magnetron anode and cathode terminals. For maximum efficiency, the current source is provided by a switched mode power supply operating in a continuous current mode. A series current-smoothing inductance in the inverter supply is fed from a buck regulator device. Referring to FIG. 9, which is a simplified circuit diagram, the buck regulator comprises a MOSFET 230, the current-smoothing inductor 232 (here in the region of 500 μH), and a diode 234. The buck regulator, as shown, is connected between the 350V DC rail of the PSU output 210P (see FIG. 8) and a bridge arrangement of four switching MOSFETs 236 to 239, forming an inverter stage. These transistors 236 to 239 are connected in an H-bridge and are operated in anti phase with slightly greater than 50% ON times to ensure a continuous supply current to the primary winding 240P of the step-up transformer 240. A bridge rectifier 242 coupled across the secondary winding 240F and a relatively small smoothing capacitor 244, having a value less than or equal to 220 μS yields the required high voltage supply 200P for the magnetron.

By pulsing the buck transistor 230 as a switching device at a frequency significantly greater than the repetition frequency of the treatment pulses, which is typically between 1 and 10 Hz or 15 Hz, and owing to the effect of the inductor 232, continuous current delivery at a power level in excess of 1 kW can be provided for the magnetron within each treatment pulse. The current level is controlled by adjusting the mark-to-space ratio of the drive pulses applied to the gate of the buck transistor 230. The same gate terminal is used, in this case, in combination with a shut-down of the drive pulses to the inverter stage transistors, to de-activate the magnetron between treatment pulses.

It will be appreciated by the skilled man in the art that single components referred to in this description, e.g. single transistors, inductors and capacitors, may be replaced by multiple such components, according to power handling requirements, and so on. Other equivalent structures can also be used.

The pulse frequency of the buck transistor drive pulses is preferably greater than 16 kHz for inaudability (as well as for control loop response and minimum current ripple) and is preferably between 40 kHz and 150 kHz. Advantageously, the inverter transistors 236 to 239 are pulsed within the same frequency ranges, preferably at half the frequency of the buck transistor consistency between successive half cycles applied to the step-up transformer 240.

Transformer 240 is preferably ferrite cored, and has a turns ratio of 2:15.

Figure 10:
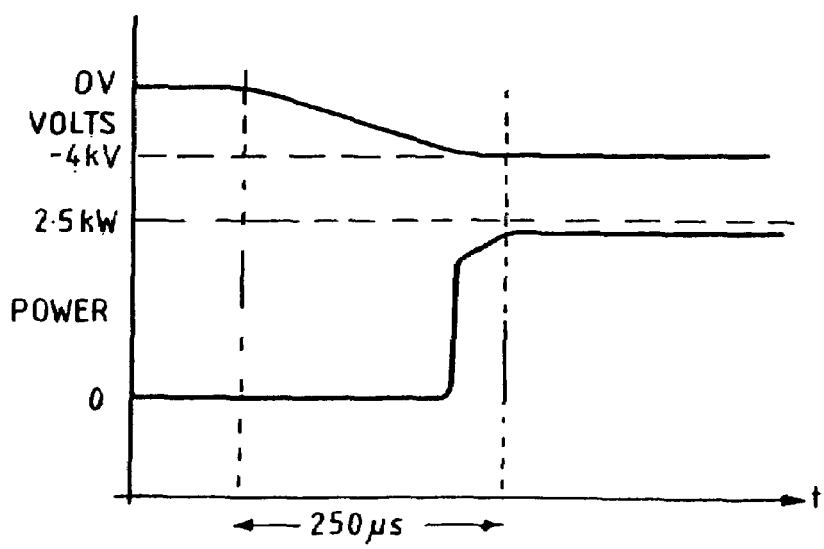
FIG. 10 is a graph illustrating the switch-on characteristics of the magnetron in the generator of FIG. 8.

As will be seen from FIG. 10, which shows the output voltage on output 200P and the power output of the magnetron at the commencement of a treatment pulse, start-up can be achieved in a relatively short time, typically less than 300 μs, depending on the vale of the capacitor 244. Switch-off time is generally considerably shorter. This yields the advantage that the treatment pulse length and, as a result, the energy delivered per treatment pulse (typically 2 to 6 joules) is virtually unaffected by limitations in the power supply or the magnetron. High efficiency (typically 80%) can be achieved for the conversion from a supply voltage of hundreds of volts (on supply rails 228 and 229) to the high voltage output 200P (see FIG. 9).

Consistent control of the magnetron power output level, with rapid response to changing load conditions, can now be achieved using feedback control of the mark-to-space ration of the drive pulses to the buck transistor 230. Since the power output from the magnetron is principally dependent on the anode to cathode current, the power supply control servos are current-based. These include a control loop generating an error voltage from a gain-multiplied difference between measured anode to cathode current and a preset output-power-dependent current demand. The voltage error is compensated for the storage inductor current and the gain multiplied difference determines the mark-to-space ratio of the driving pulses supplied to the buck transistor 230, as shown in the control loop diagrams of FIGS. 11 and 12.

A current-based servo action is also preferred to allow compensation for magnetron ageing resulting in increasing anode-to-cathode impedance. Accordingly, the required power delivery levels are maintained up to magnetron failure.

Figure 11:
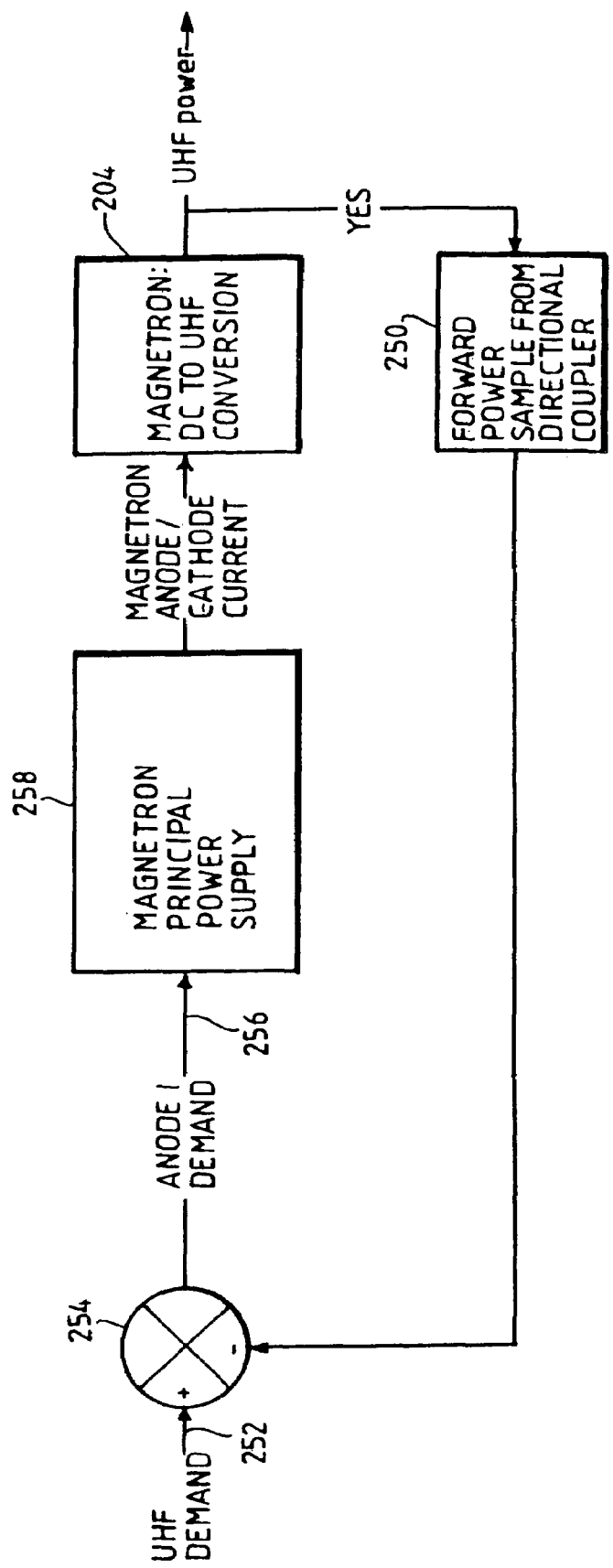
FIG. 11 is a block diagram of an outer power control loop of the generator of FIG. 8.

Referring to FIGS. 8 and 11, variations in magnetron output power with respect to anode/cathode current, e.g. due to magnetron ageing, are compensated in the controller 110 for by comparing a forward power sample 250 (obtained on line 116 in FIG. 8) with a power reference signal 252 in comparator 254. The comparator output is used as a reference signal 256 for setting the magnetron anode current, this reference signal 256 being applied to elements of the controller 110 setting the duty cycle of the drive pulses to the buck transistor 230 (FIG. 9), represented generally as the "magnetron principal power supply" block 258 in FIG. 11.

Figure 12:
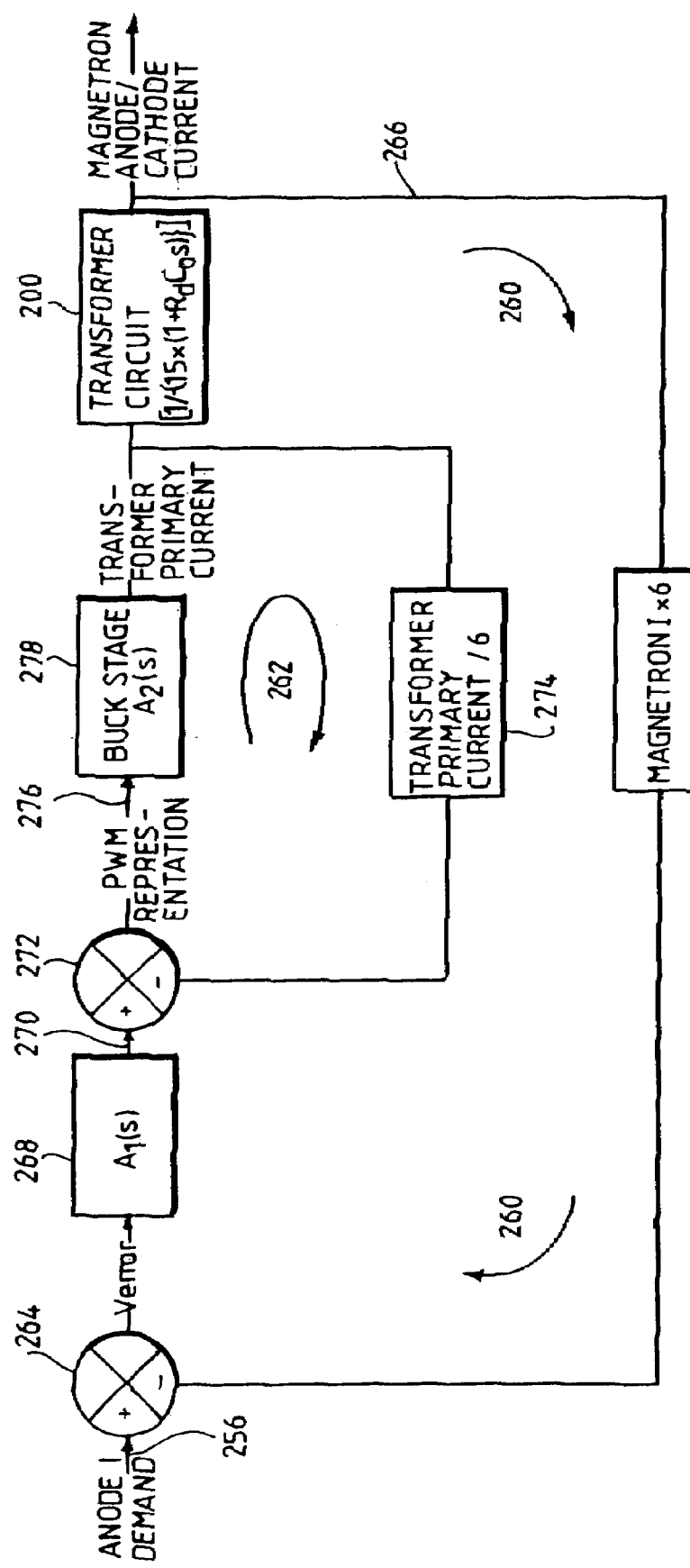
FIG. 12 is a block diagram of intermediate and inner power control loops of the generator of FIG. 8.

Referring to FIG. 12, that principal power supply block 258 has outer and inner control loops 260 and 262. The anode current reference signal 256 is compared in comparator 264 with an actual measurement 266 of the current delivered to the magnetron anode to produce an error voltage $V_{error}$. This error voltage is passed through a gain stage 268 in the controller 110 and yields a pulse width modulation (PWM) reference signal at an input 270 to a further comparator 272, where it is compared with a representation 274 of the actual current in the primary winding of the step-up transformer (see FIG. 9). This produces a modified (PWM) control signal on line 276 which is fed to the gate of the buck transistor 230 seen in FIG. 9, thereby regulating the transformer primary current through operation of the buck stage 278.

The inner loop 262 has a very rapid response, and controls the transformer primary current within each cycle of the 40 kHz drive pulse waveform fed to the gate terminal 276 of the buck transistor 230. The outer loop 260 operates with a longer time constant during each treatment pulse to control the level of the magnetron anode/cathode current. It will be seen that the combined effect of the three control loops appearing in FIGS. 11 and 12 is consistent and accurate control of anode current and output power over a full range of time periods, i.e. short term and long term output power regulation is achieved.

The actual power setting applied to the UHF demand input 252 of the outermost control loop, as shown in FIG. 11, depends on user selection for the required severity of treatment. Depth of effect can be controlled by adjusting the duration of the treatment pulses, 6 to 20 ms being a typical range.

The control connection between the controller 110 and the high voltage power supply appears in FIG. 8 as a control and feedback channel 280.

It is also possible to control heater of current by a demand/feedback line 282, e.g. to obtain the preferred steady state heater temperature.

In the case of the magnetron having an electromagnet, variation of the magnetic field strength applied to the magnetron cavity provides another control variable (as shown in FIG. 8), e.g. should lower continuous power levels be requires.

Return loss monitored by line 116 in FIG. 8 is a measure of how much energy the load reflects back to the generator. At perfect match of the generator to the load, the return loss is infinite, while an open circuit or short circuit load produces a zero return loss. The controller may therefore employ a return loss sensing output on line 116 as a means of determining load match, and in particular as a means of identifying an instrument or cable fault. Detection of such a fault may be used to shut down the output power device, in the case of the magnetron 204.

Figure 13:
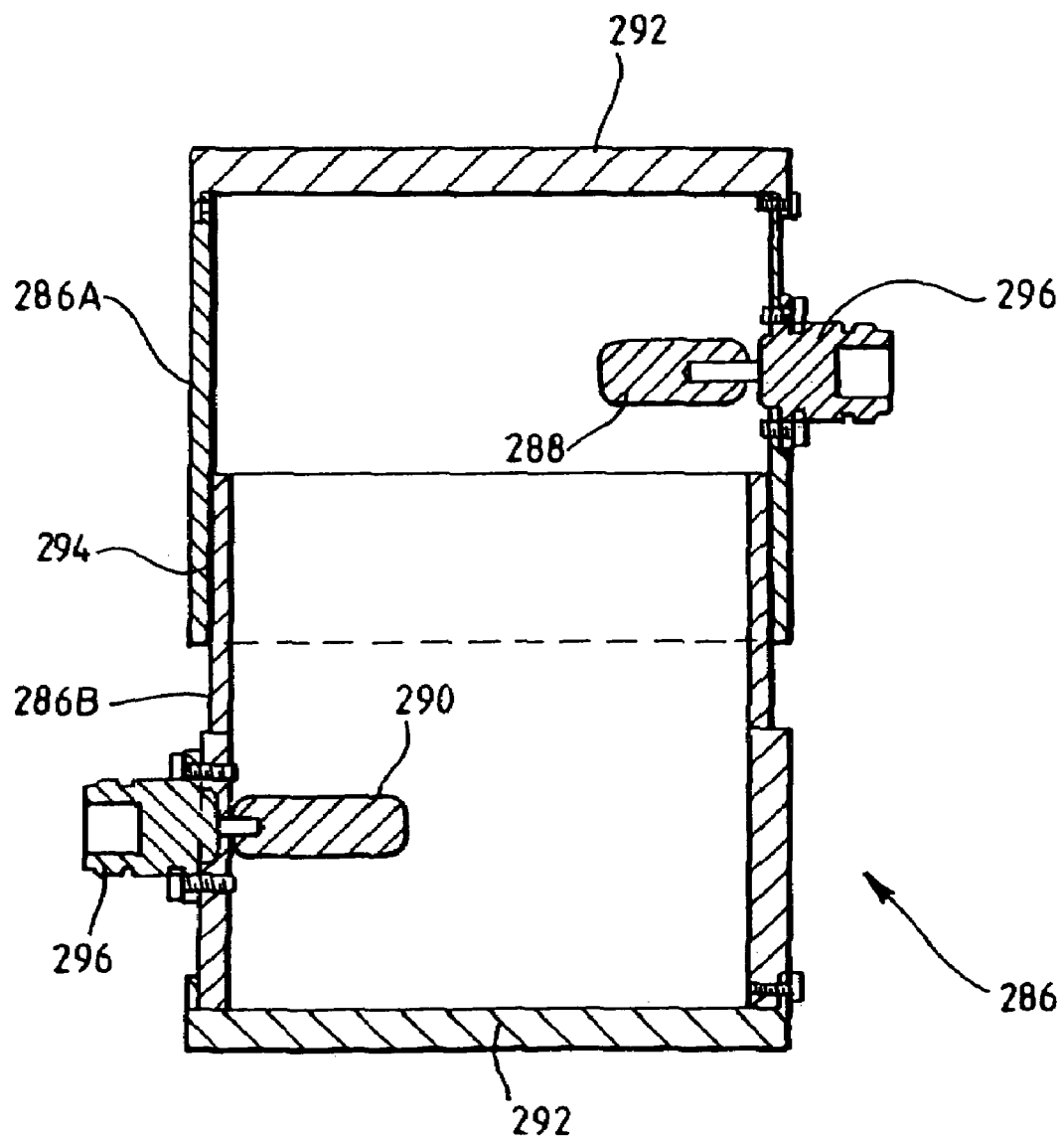
FIG. 13 is a cross section of a UHF isolator forming part of the generator of FIG. 8.

The UHF isolation stage 214 shown in FIG. 8 is illustrated in more detail in FIG. 13. As a particular aspect of the invention, this isolation stage, which is applicable generally to electrosurgical (i.e. including tissue resurfacing) devices operating at frequencies in the UHF range and upwards, has a waveguide section 286 and, within the waveguide section, spaced-apart ohmically separate launcher and collector probes 288, 290 for connection to the radio frequency power device (in this case the magnetron) and an output, specifically the output connector 216 shown in FIG. 8 in the present case. In the present example, the waveguide section is cylindrical and has end caps 292 on each end. DC isolation is provided by forming the waveguide section 286 in two interfitting portions 286A, 286B, one portion fitting within and being overlapped by the other portion with an insulating dielectric layer 294 between the two portions in the region of the overlap. Suitable connectors, here coaxial connectors 296 are mounted in the wall of the waveguide section for feeding radio frequency energy to and from the probe 288, 290.

As an alternative, the waveguide may be rectangular in cross section or may have another regular cross section.

Each probe 288, 290 is an E-field probe positioned inside the waveguide cavity as an extension of its respective coaxial connector inner conductor, the outer conductor being electrically continuous with the waveguide wall. In the present embodiment, operable in the region of 2.45 GHz, the diameter of the waveguide section is in the region of 70 to 100 mm, specifically 86 mm in the present case. These and other dimensions may be scaled according to the operating frequency.

The length of the interior cavity of the waveguide section between the probe 288, 290 is preferably a multiple of $\lambda_g/2$ where $\lambda_g$ is the guide wavelength within the cavity. The distance between each probe and its nearest end cap is in the region of an odd multiple of $\lambda_g/4$ (in the present case 32 mm), and the axial extent of the overlap between the two waveguide portions 286A, 286B should be at least $\lambda_g/4$. A typical low loss, high voltage breakdown material for the dielectric layer 294 is polyimide tape.

It will be appreciated that the isolation stage provides a degree of bandpass filtering in that the diameter of the waveguide section imposes a lower frequency limit below which standing waves cannot be supported, while high-pass filtering is provided by increasing losses with frequency. Additional bandpass filtering characteristics are provided by the relative spacings of the probe and the end caps. Note that the preferred length of the waveguide section between the end caps 292 is about $\lambda_g$. Additional filter structures may be introduced into the waveguide section to provide preferential attenuation of unwanted signals.

The isolation stage forms an isolation barrier at DC and at AC frequencies much lower than the operating frequency of the generator and can, typically, withstand a voltage of 5kV DC applied between the two waveguide portions 286A, 286B.

At low frequencies, the isolation stage represents a series capacitor with a value less than 1 μF, preventing thermionic current or single fault currents which may cause unwanted nerve stimulation. Lower values of capacitance can obtained by reducing the degree of overlap between the waveguide section portions 286A, 286B, or by increasing the clearance between them where they overlap.

Significant reductions in size of the isolation stage can be achieved by filling the interior cavity with a dielectric material having a relative dielectric constant greater than unity.

As an alternative to the E-field probes 288, 290 illustrated in FIG. 13, waves may be launched and collected using H-field elements in the form of loops oriented to excite a magnetic field.

Figure 6:
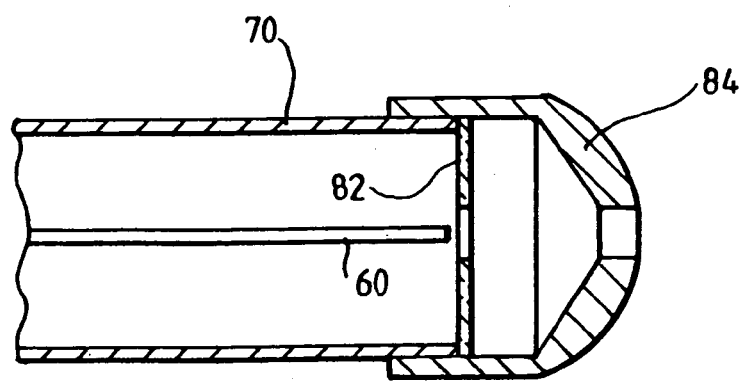
FIG. 6 is a cross-section showing a modification of part of the instrument shown in FIG. 3.

Referring now to FIG. 14, an instrument for use with a generator having a magnetron power output device comprises, as with the instrument of FIGS. 2, 3 and 6, an outer shaft 30, connector 26, coaxial feed cable 40. A transitional impedance matching structure includes a low impedance section 92 and a high impedance section 94, and provides a match between the power output device of the generator and the load provided by the plasma, which is created in an electric field between a central disc electrode 160 and an outer electrode 70 provided by a section of the conductive sleeve adjacent the disc electrode 160. Gas passes from the inlet port 32 and along the annular conduits 38A, B formed between the inner and outer conductors of the sections 92, 94 of matching structure through the electric field between the electrodes 160, 70 and is converted into a plasma under the influence of the electric field. A tubular quartz insert 180 is situated against the inside of the sleeve 50, and therefore between the electrodes 160, 70. Quartz is a low loss dielectric material, and the insert has the effect of intensifying the electric field between the electrodes, effectively bringing them closer together, while simultaneously preventing preferential arcing between them, thereby producing a more uniform beam of plasma In this embodiment, the inner electrode 160 is a disc, and is mounted directly onto the inner conductor 54 of the high impedance matching section, the latter having a length which in electrical terms is one quarter of a wavelength of the generator output. The disc electrode 160, because of its relatively small length, is, when considered in combination with the electrode 70 effectively a discrete or "lumped" capacitor, which, in conjunction with the inherent distributed inductance of the inner conductor 54 forms a series resonant electrical assembly. The shape of the disc electrode 160 also serves to spread the plasma output beam, thereby increasing the "footprint" of the beam on tissue, this can be desirable in skin resurfacing since it means that a given area of tissue can be treated with fewer "hits" from the instrument. The voltage step-up which occurs in this resonant structure is lower in the instrument of this embodiment than with the instrument of FIGS. 2, 3 and 6, and so the step-up of the generator output voltage at the electrodes 160, 70 as a result of resonance within the resonant assembly is correspondingly lower. One reason for this is that a magnetron power output device produces a significantly higher level of power and at a higher voltage (typically 300 Vrms), and therefore it is not necessary to provide such a high step-up transformation, hence the lower Q of the resonant assembly.

Figure 15:
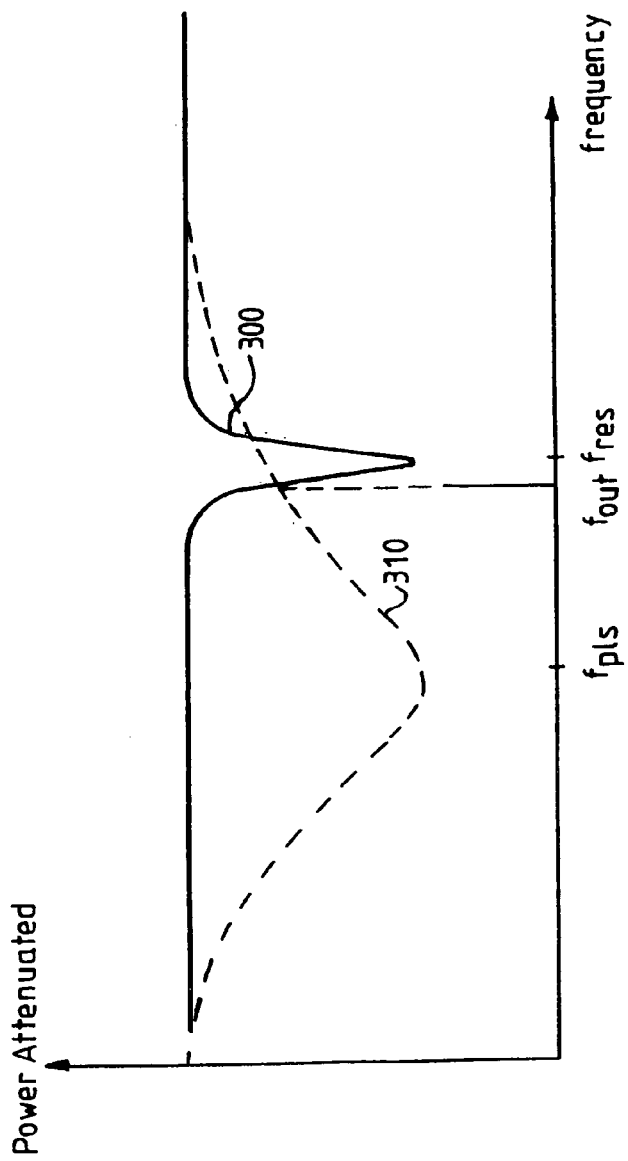
FIG. 15 is a graph of reflected power versus frequency for the instrument of FIG. 14 when employed with the generator of FIG. 7.

Tuning of the output frequency of the magnetron power output device is difficult. Nonetheless, the resonant frequency of the instrument undergoes a shift once a plasma has been struck as a result of a lowering of the load impedance (due to the higher conductivity of plasma than air), so the problem of optimum power delivery for plasma ignition on the one hand and plasma maintenance on the other still applies. Referring to FIG. 15, the reflected power dissipated within the instrument prior to plasma ignition with varying frequency is illustrated by the line 300. It can be seen that the resonance within the instrument occurs at a frequency $f_{res}$, represented graphically by a sharp peak, representative of a relatively high quality factor Q for the voltage multiplication, or upward transformation that occurs within the instrument at resonance. The reflected power versus frequency characteristic curve for the instrument once a plasma has been struck is illustrated by the line 310, and it can be seen that the resonant frequency of the instrument once a plasma has been created $f_{pls}$ is lower than that prior to ignition, and that the characteristic curve has a much flatter peak, representative of lower quality factor Q. Since the magnetron power output device is relatively powerful, one preferred mode of operation involves selecting a resonant frequency of the instrument such that the output frequency of the magnetron power output device is operable both to benefit from resonance within the instrument to strike a plasma, and also to maintain a plasma.

Referring again to FIG. 15 the magnetron power output device has an output frequency $f_{out}$ which lies between the resonant frequencies $f_{res}$ and $f_{pls}$. The frequency $f_{out}$ is shifted from the resonant frequency $f_{res}$ as far as possible in the direction of the resonant frequency $f_{pls}$ in an attempt to optimise the delivery of power into the plasma, while still ensuring that sufficient resonance occurs within the instrument at $f_{out}$ to strike a plasma. This compromise in the output frequency of the magnetron power output device is possible as a result of the relatively large power output available, meaning that significantly less resonance is required within the instrument, either in order to strike a plasma or subsequently to maintain a plasma, than would be the case with lower power output devices.

Figure 16:
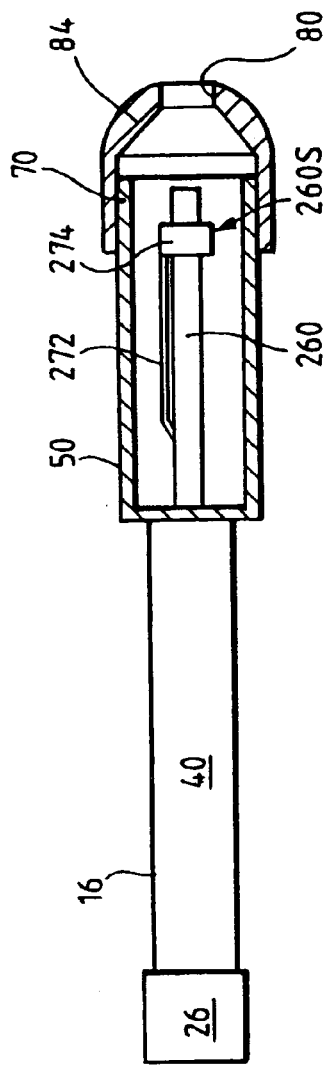
FIG. 16 is a section through a further embodiment of instrument.

In a further embodiment, the instrument is constructed so that it incorporates two resonant assemblies: one which is resonant prior to the ignition of a plasma and the other which is resonant subsequent to ignition, wherein both of the resonant assemblies have similar or substantially the same resonant frequency. With an instrument of this type it is then possible to optimise power delivery for ignition and maintenance of a plasma at a single frequency. Referring now to FIG. 16, an instrument 16 has a connector 26 at its distal end, a coaxial feed structure 40 extending from the connector 26 to a bipolar electrode structure comprising a rod-like inner electrode 260 and an outer electrode 70 provided by a section of outer conductive sleeve 50 lying adjacent the rod electrode 260, A conductive end cap 84 defines an aperture 80 through which plasma passes, and helps to intensify the electric field through which the plasma passes, thereby enhancing the ease of power delivery into the plasma. The characteristic impedance of the section of transmission line formed by the electrode structure 260, 70 is chosen to provide matching between the power output device and the load provided by the plasma. As will be explained subsequently, it is believed that the plasma load in this embodiment has a lower impedance than in previous embodiments, which therefore makes matching easier. In addition the instrument comprises an auxiliary or strike electrode 260S. The strike electrode 260S comprises two elements: a predominantly inductive element, provided in this example by a length of wire 272 connected at its proximal end to the proximal end of rod electrode, and a predominantly capacitive element in series with the inductive element, which is provided in this example by a ring 274 of conductive material connected to the distal end of the wire 272, and which extends substantially coaxially with the rod electrode 260, but is spaced therefrom.

Figure 17:
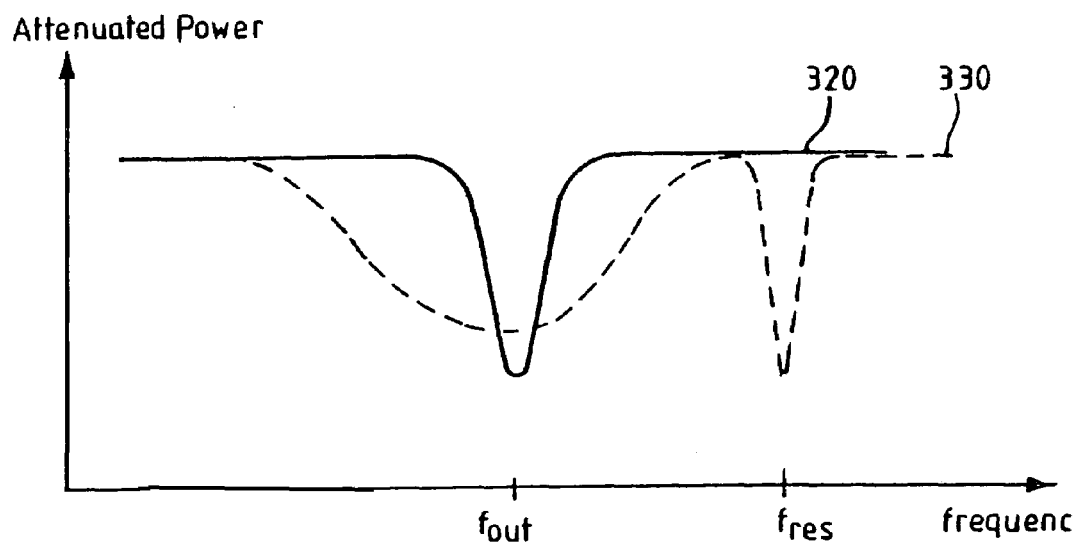
FIG. 17 is a graph of reflected power versus frequency in the instrument of FIG. 16.

Referring now to FIG. 17, the structure of the strike electrode 260S is such that the inductance in the form of the wire 272 and the capacitance in the form of the ring 274 forms a resonant assembly which is resonant at the output frequency of the generator $f_{out}$, and the characteristic variation of reflected power with input frequency for the strike electrode 260S is illustrated by the line 320. By contrast, the transmission line formed by the electrode structure 260, 70 (whose characteristic variation of reflected power with input frequency is illustrated by the line 330), has, prior to the ignition of a plasma, a resonant frequency $f_{res}$ that is significantly higher than the generator output frequency to an extent that little or no resonance will occur at that frequency. However, the electrode structure 260, 70 is configured such that, once a plasma has been formed (which can be thought of as a length of conductor extending from the rod electrode 260 out of the aperture 80), it is a resonant structure at the output frequency of the generator, albeit a resonance at a lower Q. Thus, prior to the formation of a plasma, the strike electrode 260S is a resonant assembly which provides voltage multiplication (also known as step-up transformation) of the generator output signal, whereas subsequent to the formation of a plasma the electrode structure 260, 70 is a resonant assembly which will provide voltage multiplication. The electrode structure 260S, 70 may be thought of as having a length, in electrical terms, and once a plasma has been created (and therefore including the extra length of conductor provided by the plasma) which is equal to a quarter wavelength, and so provides a good match of the generator output.

When the generator output signal passes out of the coaxial feed structure 40 the signal initially excites the strike electrode 260S into resonance since this is resonant at the output frequency of the generator, but does not excite the electrode structure 260, 70, since this is not resonant at the output frequency of the generator until a plasma has been created. The effect of a resonance (and therefore voltage multiplication) in the strike electrode 260S which does not occur in the electrode structure 260, 70 is that there is a potential difference between the strike electrode 260S and the rod electrode 260. If this potential difference is sufficiently large to create an electric field of the required intensity between the strike electrode 260S and the rod electrode 260 (bearing in mind that, because of the relatively small distance between the electrodes 260S and 260, a relatively low potential difference will be required), a plasma is created between the electrodes. Once the plasma has been created, the plasma will affects the electrical characteristics of the electrode structure such that it is resonant at the generator output frequency (or frequencies similar thereto), although this resonance will be not be as pronounced because the Q of the resonant assembly when a plasma has been created is lower than the Q of the strike electrode 260S.

It is not essential that the strike electrode 260S and an "ignited" electrode structure 260, 70 (i.e. the electrode structure 260, 70 with a created plasma) have identical resonant frequencies in order to benefit from this dual electrode ignition technique, merely that they are each capable of interacting with the generator output to strike and then maintain a plasma without having to retune the generator output. Preferably, however, the resonant frequencies should be the same to within the output frequency bandwidth of the generator. For example, if the generator produced an output of 2450 MHz and at this frequency this output had an inherent bandwidth of 2 MHz, so that, in effect, at this selected frequency the generator output signal is in the frequency range 2449-2451 MHz, the two resonant frequencies should both lie in this range for optimum effect.

Figure 18:
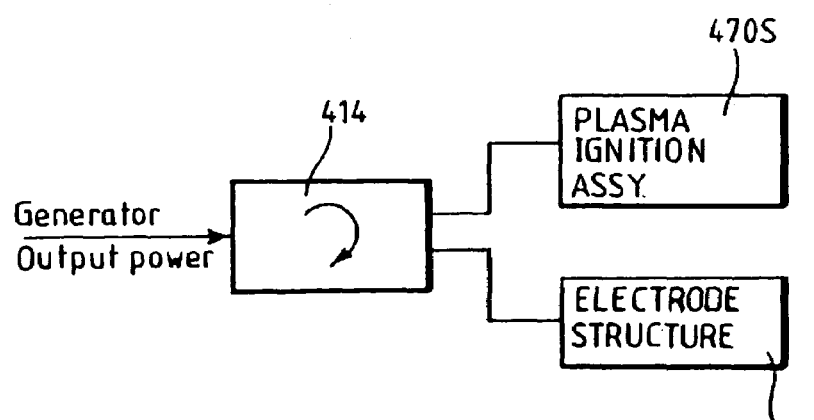
FIG. 18 is a schematic illustration of a further embodiment of instrument.
Figure 23:
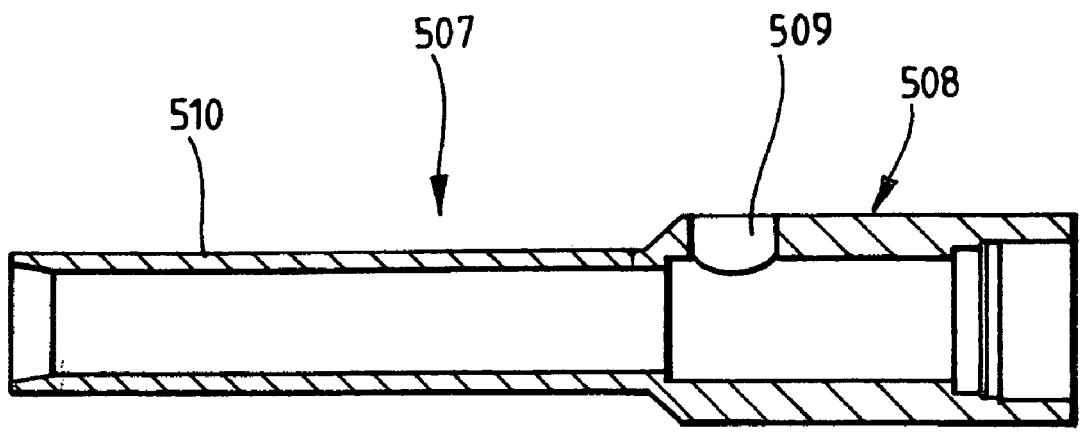
FIG. 23 is a sectional side view of an electrode used in the instrument of FIG. 21.
Figure 24:
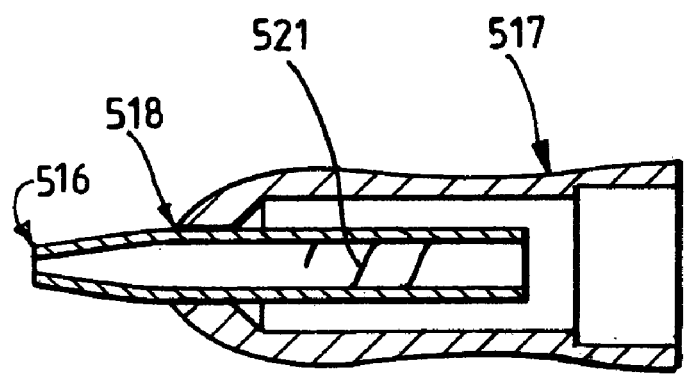
FIG. 24 is a sectional side view of a disposable assembly, used in the instrument of FIG. 21.

Referring now to FIG. 18, in a further embodiment which provides independent ignition of the plasma, an instrument includes a plasma ignition assembly 470S and an electrode structure 470 which are separately wired (and mutually isolated) to a circulator 414 within the instrument. Output signals from the generator pass initially into the circulator 414. The circulator passes the output signals preferentially into the output channel providing the best match to the generator. As with the previous embodiment, prior to ignition of a plasma, the match into the electrode structure 470 is poor, whereas the ignition assembly is configured to provide a good match prior to ignition, and so the generator output is passed by the circulator into the ignition assembly 470S. Since it is wired independently, the ignition assembly 470 may be provided by any suitable spark or arc generator which is capable of producing a spark or arc with power levels available from the generator. For example, the ignition assembly can include a rectifying circuit and a DC spark generator, a resonant assembly to provide voltage multiplication as in the embodiment of FIG. 16 or any other suitable spark or arc generator. Once ignition of the plasma has occurred, the resultant change in the electrical characteristics of the electrode structure cause matching of the generator output into the electrode structure, and so the circulator then acts to divert the generator output into the electrode structure to enable delivery of power into the plasma.

In the majority of embodiments of the surgical system described above an oscillating electric field is created between two electrodes, both of which are substantially electrically isolated from the patient (inevitably there will be an extremely low level of radiation output from the instrument in the direction of the patient, and possibly some barely detectable stray coupling with the patient), whose presence is irrelevant to the formation of a plasma A plasma is struck between the electrodes (by the acceleration of free electrons between the electrodes) and the plasma is expelled from an aperture in the instrument, primarily under the influence of the pressure of gas supplied to the instrument. As a result, the presence of a patient's skin has no effect on the formation of a plasma (whereas in the prior art a plasma is struck between an electrode within an instrument and the patient's skin) and the patient does not form a significant conductive pathway for any electrosurgical currents.

In a particularly preferred instrument best suited to operation with a high output power generator such as the above-described generator embodiments having a magnetron as the output power device, a dual matching structure such as those included in the instrument embodiments described above with reference to FIGS. 2 and 14, is not required. Referring to FIGS. 19 and 20, this preferred instrument comprises a continuous conductive sleeve 50 having its proximal end portion fixed within and electrically connected to the outer screen of a standard (N-type) coaxial connector, and an inner needle electrode 54 mounted in an extension 42 of the connector inner conductor. Fitted inside the distal end portion 70 of the sleeve outer conductor 50 is a heat resistant dielectric tube 180 made of a low loss dielectric material such as quartz. As shown in FIGS. 19 and 20, this tube extends beyond the distal end of the sleeve 50 and, in addition, extends by a distance of at least a quarter wavelength (the operating wavelength λ) inside the distal portion 70. Mounted inside the quartz tube where it is within the distal end portion 70 of the sleeve 50 is a conductive focusing element 480 which may be regarded as a parasitic antenna element for creating electric field concentrations between the needle electrode 54 and the distal end portion 70 of the sleeve 50.

Adjacent the connector 26, the sleeve 50 has a gas inlet 32 and provides an annular gas conduit 38 extending around the inner conductor extension 42, the needle electrode 8, and distally to the end of the quartz tube 180, the latter forming the instrument nozzle 180N. A sealing ring 482 prevents escape of gas from within the conduit 38 into the connector 26.

When connected to a coaxial feeder from a generator such as that described above with reference to FIG. 8, the proximal portion of the instrument, comprising the connector 26 and the connector inner conductor extension 42, constitutes a transmission line having a characteristic impedance which, in this case, is 50 ohms. A PTFE sleeve 26S within the connector forms part of the 50 ohms structure.

The needle electrode 54 is made of heat resistant conductor such as tungsten and has a diameter such that, in combination with the outer sleeve 50, it forms a transmission line section of higher characteristic impedance than that of the connector 26, typically in the region of 90 to 120 ohms. By arranging for the length of the needle electrode, i.e. the distance from the connector inner conductor extension 42 to its tip 54T (see FIG. 20), to be in the region of λ/4, it can be made to act as an impedance transformation element raising the voltage at the tip 54T to a level significantly higher than that seen on the 50 ohms section (inner conductor extension 42). Accordingly, an intense E-field is created between the tip 54T of the inner electrode needle and the adjacent outer conductor distal end portion 70. This, in itself, given sufficient input power, can be enough to create a gas plasma extending downstream from the tip 54T and through the nozzle 180N. However, more reliable striking of the plasma is achieved due to the presence of the focusing element 480.

This focussing element 480 is a resonant element dimensioned to have a resonant frequency when in-situ in the quartz tube, in the region of the operating frequency of the instrument and its associated generator. As will be seen from the drawings, particularly by referring to FIG. 20, the resonant element 480 has three portions, i.e. first and second folded patch elements 480C, folded into irregular rings dimensioned to engage the inside of the quartz tube 180, and an interconnecting intermediate narrow strip 480L. These components are all formed from a single piece of conductive material, here spring stainless steel, the resilience of which causes the element to bear against tube 180.

It will be appreciated that the rings 480C, in electrical terms, are predominately capacitive, whilst the connecting strip 480L is predominately inductive. The length of the component approaches λ/4. These properties give it a resonant frequency in the region of the operating frequency and a tendency to concentrate the E-field in the region of its end portions 480C.

In an alternative embodiment (not shown) the focussing element may be a helix of circular or polygonal cross section made from, e.g. a springy material such as tungsten. Other structures may be used.

The focussing element is positioned so that it partly overlaps the needle electrode 54 in the axial direction of the instrument and, preferably has one of the regions where it induces high voltage in registry with the electrode tip 54T.

It will be understood by those skilled in the art that at resonance the voltage standing wave on the focussing element 480 is of greatest magnitude in the capacitive regions 480C. The irregular, folded, polygonal shape of the capacitive sections 480C results in substantially point contact between the focussing element and the inner surface of the quartz tube 180. This property, together with the E-field concentrating effect of the resonator element structure and the presence close by of the high dielectric constant material of the inserted tube 180, all serve to maximise the filed intensity, thereby to ensure striking of a plasma in gas flowing through the assembly.

In practice, arcing produced by the focussing element 480 acts as an initiator for plasma formation in the region surrounding the electrode tip 54T. Once a plasma has formed at the tip 54T it propagates along the tube, mainly due to the flow of gas towards the nozzle 180N. Once this has happened, the instrument presents an impedance match for the generator, and power is transferred to the gas with good efficiency.

One advantage of the focussing element is that its resonant frequency is not especially critical, thereby simplifying manufacture.

Referring to FIGS. 21 to 24, an instrument 500 for use in the surgical system described above with reference to FIG. 1 comprises two interconnecting sections, a handpiece 501 and a disposable assembly 502. The instrument 500 comprises a casing 503, closed at the rear by an end cover 504, through which is fed a coaxial cable 505. The central conductor of the coaxial cable 505 is connected to an inner electrode 506, formed of Molybdenum. The outer conductor of the coaxial cable is connected to an outer electrode 507, shown in FIG. 23. The outer electrode comprises a hollow base portion 508, with a gas inlet hole 509 formed therein, and a tubular extension 510 extending from the base portion. The inner electrode extends longitudinally within the outer electrode 507, with dielectric insulators 511 and 512 preventing direct electric contact therebetween.

A gas inlet 513 passes through the end cover 504, and communicates via a lumen 514 within the casing, through the gas inlet hole 509 in the outer electrode, and through further channels 515 in the insulator 512, exiting in the region of the distal end of the inner electrode 506.

The disposable assembly 502 comprises a quartz tube 516, mounted within a casing 517, a silicone rubber washer 518 being located between the casing and the tube. The casing 517 has a latch mechanism 519 such that it can be removably attached to the casing 503, via a corresponding detent member 520. When the disposable assembly 502 is secured to the handpiece 501, the quartz tube 516 is received within the handpiece, such that the inner electrode 506 extends into the tube, with the tubular extension 510 of the outer electrode 507 extending around the outside of the tube 516.

A resonator in the form of a helically wound tungsten coil 521 is located within the tube 516, the coil 521 being positioned such that, when the disposable assembly 502 is secured in position on the handpiece 501, the proximal end of the coil is adjacent the distal end of the inner electrode 506. The coil is wound such that it is adjacent and in intimate contact with the inner surface of the quartz tube 516.

In use a gas, such as nitrogen, is fed through the gas inlet 513, and via lumen 514, hole 509, and channels 519 to emerge adjacent the distal end of the inner electrode 506. A radio frequency voltage is supplied to the coaxial cable 505, and hence between electrodes 506 and 507. The coil 521 is not directly connected to either electrode, but is arranged such that it is resonant at the operating frequency of the radio frequency voltage supplied thereto. In this way, the coil 521 acts to promote the conversion of the gas into a plasma, which exits from the tube 516 and is directed on to tissue to be treated.

The parameters of the helical coil 521 that affect its resonant frequency include the diameter of the wire material used to form the coil, its diameter, pitch and overall length. These parameters are chosen such that the coil has its resonant frequency effectively at the operating frequency of the signal applied to the electrodes. For a 2.47 GHz operating frequency (and a free-space wavelength of approximately 121 mm), a resonator coil was employed having an approx coil length of 13 mm, a pitch of 5.24 mm, outer diameter 5.43 mm, wire diameter of 0.23 mm, and overall wire length of 41.8 mm. This gives a coil with a resonant frequency of approx 2.517 GHz (the difference allowing for the different speeds of propagation of e/m radiation in air and quartz respectively).

Following repeated use of the instrument, the resonant coil 521 will need to be replaced on a regular basis. The arrangement described above allows for a disposable assembly to be provided which is quick and easy to attach and detach, and also repeatedly provides the accurate location of the resonant coil 521 with respect to the electrode 506.

Figure 25:
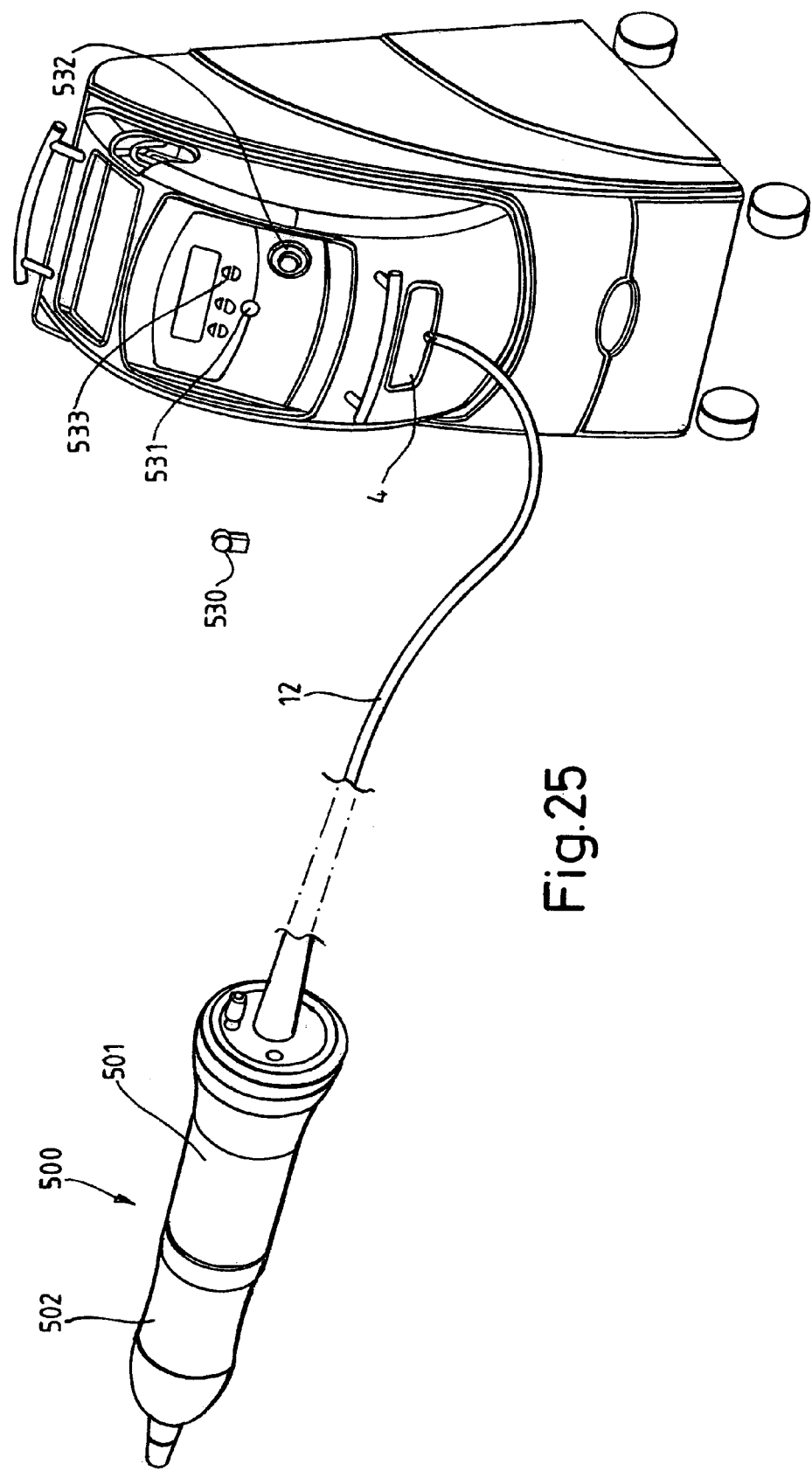
FIG. 25 is a schematic illustration of a system according to a further aspect of the invention.

Referring to FIG. 25, an electrosurgical system is shown comprising a generator 4, and an instrument 500 connected to the generator by means of a cable 12. The instrument 500 comprises a re-usable handpiece 501 and a disposable assembly 502, as previously described. The handpiece may be stored in a holder 532 present on the generator 4 when not in use.

The disposable assembly is delivered to the user in a sealed package containing the assembly 502 and a button 530. The button 530 is an electronic key such as that obtained from Dallas Semiconductor Corp and known by the trademark "i-button".

When the user attaches a new disposable assembly 502 to the handpiece 501, they also connect the button 530 to a reader 531 present on the generator 4. The button 530 contains a unique identifying code which is read by the reader 531 and confirmed by the generator 4. If the code carried by the button is not a recognisable or valid code, the generator does not supply pulses of energy to the handpiece. If the code is recognised as a valid code, the generator supplies pulses of energy to the handpiece 501. The generator sends information to the button 530 concerning the time at which the pulses of energy are first supplied, this information being written to and stored on the button 530.

The pulses of energy supplied by the generator 4 to the handpiece 501 can be adjusted by the user so as to be at different energy level settings. This adjustment is carried out by means of user interface 533 present on the generator 4. The generator sends a signal to the button 530 updating an incremental counter every time a series of 10 pulses are supplied to the handpiece 501. (If there is sufficient memory capability in the button 530, the generator can send a signal for each pulse of energy supplied). The generator increments the counter by 1 unit for each pulse supplied the energy of which is less than 2 Joules, and by 2 units for each pulse the energy of which is greater than 2 Joules. The increments are written to the button 530 and stored thereon. When the incremental counter reaches a maximum value, say 2,400 units, the supply of energy to the handpiece is halted and a signal is displayed indicating that the disposable assembly 502 must be replaced.

To obtain further treatment pulses, a new pack containing a fresh disposable assembly must be opened, and the new button presented to the reader on the generator. This ensures that the disposable assembly is replaced before the resonant coil 521 degrades to an unacceptable level. The incrementing of the counter takes into account that the degradation will occur more quickly with higher energy pulses than with lower energy pulses.

It is often the case that the apparatus of FIG. 25 may be used to give repeated treatment sessions to a particular patient. In this case the button 530 is removed from the reader 531, and re-presented at some later time. The reader 531 will then read from the button 530 the value of the incremental counter, and calculate whether the incremental counter is at its maximum value. If the counter is below the maximum value, treatment is allowed to continue.

As the value for the incremental counter is stored on the button 530 as opposed to being stored in the generator 4, the validation will be performed even if the button 530 is presented to a different generator, say at a different location. This is not the case with various prior art systems in which all of the information on past usage is stored in the generator itself. This prevents the usage-limitation being circumvented by simply taking the button to a different generator, and also allows the legitimate situation where a patient may conceivably attend different sites for subsequent treatments.

In addition to preventing the operation of the handpiece once the usage limit has been reached, the system may also prevent further operation if the button 530 is presented to the reader 531 after a period of time following the first use of the disposable assembly 502. As stated previously, the time of first use is written to the button 530. If, when the button is presented again, a predetermined period of time has elapsed (say 10 hours), then further operation of the handpiece is prevented.

As mentioned above, the use of UHF signals is not essential to the operation of the present invention, and the invention may be embodied at any frequency from DC signals upwards. However, the use of UHF signals has an advantage in that components whose length is one quarter wavelength long may be incorporated within compact surgical instruments to provide voltage transformation or matching. In addition several instruments have been illustrated which have resonant assemblies for the purpose of step-up voltage transformation, but this is not essential, and upward voltage transformation can be performed within an instrument without making use of resonance.

If the instruments disclosed herein are intended for clinical use, it is possible to sterilise them, and this may be performed in a number of ways which are known in the art, such as the use of gamma radiation, for example, or by passing a gas such as ethylene oxide through the instrument (which will ensure that the conduit for the gas is sterilised). The sterilised instruments will then be wrapped in a suitable sterile package which prevents the ingress of contagion therein.

The various modifications disclosed herein are not limited to their association with the embodiments in connection with which they were first described, and may be applicable to all embodiments disclosed herein.

What is claimed is:

1. A system for controlling the use of a device for treating human tissue, the system comprising:

a generator for providing pulses of energy to the device, the pulses of energy being at selected energy levels;
   a controller for controlling the supply of energy to the device;
   an electronic key associated with the device and including memory means; and
   a read/write device associated with the controller for downloading information from the electronic key and writing information to the memory means;
   the controller causing the read/write device to send signals to the memory means when energy pulses are provided to the device by the generator to cause updating of a device usage counter in the memory means, whereby the rate at which the counter is incremented increases as the delivered power is increased, the controller further causing the generator to cease the provision of pulses when the device usage counter reaches a predetermined maximum value.

2. A system according to claim 1, wherein the controller is configured to cause the read/write device to send a counter-incrementing signal to the memory means each time a predetermined amount of energy is provided to the device by the generator, and wherein the controller updates the counter by a first incremental value for every pulse provided to the device which is below a predetermined energy threshold level, and updates the counter by a second larger value for every pulse provided to the device which is above the predetermined energy threshold level.

3. A system according to claim 1, wherein the device is a gas plasma tissue treatment device.

4. A system according to claim 2, wherein the predetermined threshold energy level is in the range of 0.5 to 2.5 Joules.

5. A system according to claim 4, wherein the predetermined threshold energy level is substantially 2 Joules.

6. A system according to claim 3, wherein the second value is substantially twice the value of the first value.

7. A system according to claim 3, wherein the predetermined maximum value is between 500 and 5000 times the first value.

8. A system according to claim 7, wherein the predetermined maximum value is between 2000 and 3000 times the first value.

9. A system according to claim 1, wherein the memory means includes a unique identifying code for the electronic key.

10. A system according to claim 1, wherein the controller is adapted to cause the read/write device to send a signal to the memory means representative of the time that the key is first presented to the read/write device.

11. A system according to claim 1, wherein the controller is adapted to cause the read/write device to send a signal to the memory means representative of the time that the first pulses of energy are provided to the device.

12. A system according to claim 10, wherein the controller is adapted to compare the current time with the representative time, and to prevent the provision of pulses when the time difference exceeds a predetermined value.

13. A system according to claim 12, wherein the predetermined value is between 6 and 12 hours.

14. A method of controlling the use of a device for treating human tissue comprising the steps of:

providing a controller for controlling the supply of energy to the device, and an electronic key associated with each device, the electronic key including memory means,
   presenting the electronic key to the controller, reading the value from an incremental counter on the memory means and determining whether it has reached a predetermined maximum value, supplying pulses of energy to the device if the incremental counter has not reached its predetermined maximum value, and updating the incremental counter at a rate which increases as the power provided to the device is increased.

15. A method according to claim 14, in which the increase in the rate of incrementing the counter as the power increases is brought about by updating the incremental counter by a first value each time that a pulse or a number of pulses is provided to the device below a predetermined threshold energy level, and updating the incremental counter by a second larger value each time that a pulse or a number of pulses is provided to the device above the predetermined threshold energy level.

* * * * *